US009345388B2

(12) United States Patent
Naito

(10) Patent No.: US 9,345,388 B2
(45) Date of Patent: May 24, 2016

(54) DRIVING FORCE TRANSMITTING UNIT, INSERTION INSTRUMENT, ROTARY UNIT, INSERTION BODY ASSEMBLY, AND INSERTION DEVICE

(71) Applicant: OLYMPUS CORPORATION, Tokyo (JP)

(72) Inventor: Kimihiko Naito, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/614,617

(22) Filed: Feb. 5, 2015

(65) Prior Publication Data

US 2015/0148607 A1    May 28, 2015

Related U.S. Application Data

(63) Continuation of application No. PCT/JP2013/074293, filed on Sep. 9, 2013.

(30) Foreign Application Priority Data

Sep. 12, 2012 (JP) ................. 2012-200983
Sep. 26, 2012 (JP) ................. 2012-213062

(51) Int. Cl.
  *A61B 1/00* (2006.01)
  *G02B 23/24* (2006.01)
  *A61B 1/04* (2006.01)

(52) U.S. Cl.
  CPC .......... *A61B 1/0016* (2013.01); *A61B 1/00006* (2013.01); *A61B 1/00135* (2013.01);
  (Continued)

(58) Field of Classification Search
  CPC .......... A61B 1/00133; A61B 1/00121; A61B 1/00128; A61B 1/00073; A61B 1/00135; A61B 1/00154; A61B 1/00156
  USPC ................. 600/104, 106, 114, 117, 153–156; 604/510
  See application file for complete search history.

(56) References Cited

U.S. PATENT DOCUMENTS

2005/0272976 A1* 12/2005 Tanaka ............... A61B 1/00073
                                              600/114
2010/0240954 A1*  9/2010 Wood ..................... A61B 1/018
                                              600/114
2012/0029281 A1*  2/2012 Frassica ............. A61B 1/00082
                                              600/114

FOREIGN PATENT DOCUMENTS

JP    H06-105800 A    4/1994
JP    2000-139925 A   5/2000
(Continued)

OTHER PUBLICATIONS

English translation of International Preliminary Report on Patentability together with the Written Opinion dated Feb. 5, 2015 received in related International Application No. PCT/JP2013/074293.

(Continued)

*Primary Examiner* — Anhtuan T Nguyen
*Assistant Examiner* — Timothy J Neal
(74) *Attorney, Agent, or Firm* — Scully, Scott, Murphy & Presser, P.C.

(57) ABSTRACT

A driving force transmitting unit includes a line portion extending along a driving axis in a channel, and a slider portion attached to a proximal portion of the line portion and movable relative to the line portion along the driving axis. The driving force transmitting unit includes an urging portion contracting in response to a movement of the slider portion relative to the line portion toward a distal direction and thereby applying an urging force toward the distal direction to the line portion.

19 Claims, 21 Drawing Sheets

(52) U.S. Cl.
CPC ......... *A61B1/00154* (2013.01); *A61B 1/00156* (2013.01); *A61B 1/00158* (2013.01); *G02B 23/2476* (2013.01)

(56) References Cited

FOREIGN PATENT DOCUMENTS

| JP | 2005-253892 A | 9/2005 |
|---|---|---|
| JP | 2005-288035 A | 10/2005 |
| JP | 2007-185394 A | 7/2007 |
| JP | 2010-227170 A | 10/2010 |
| WO | WO 2013/145803 A1 | 10/2013 |
| WO | WO 2013/187446 A1 | 12/2013 |

OTHER PUBLICATIONS

International Search Report dated Nov. 26, 2013 issued in PCT/JP2013/074293.
Japanese Office Action dated May 13, 2014 issued in JP 2014-514264.

* cited by examiner

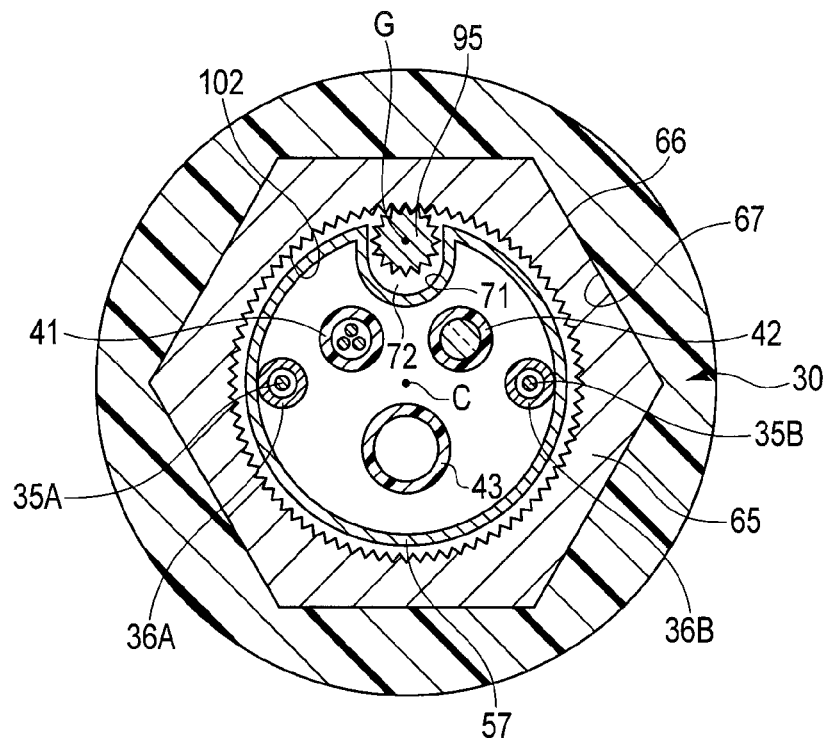
F I G. 4
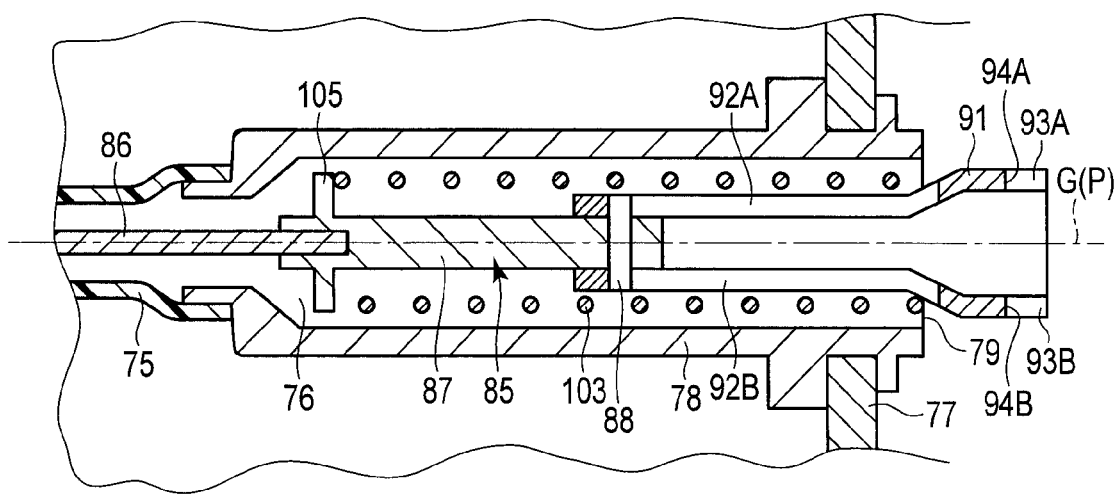
F I G. 5

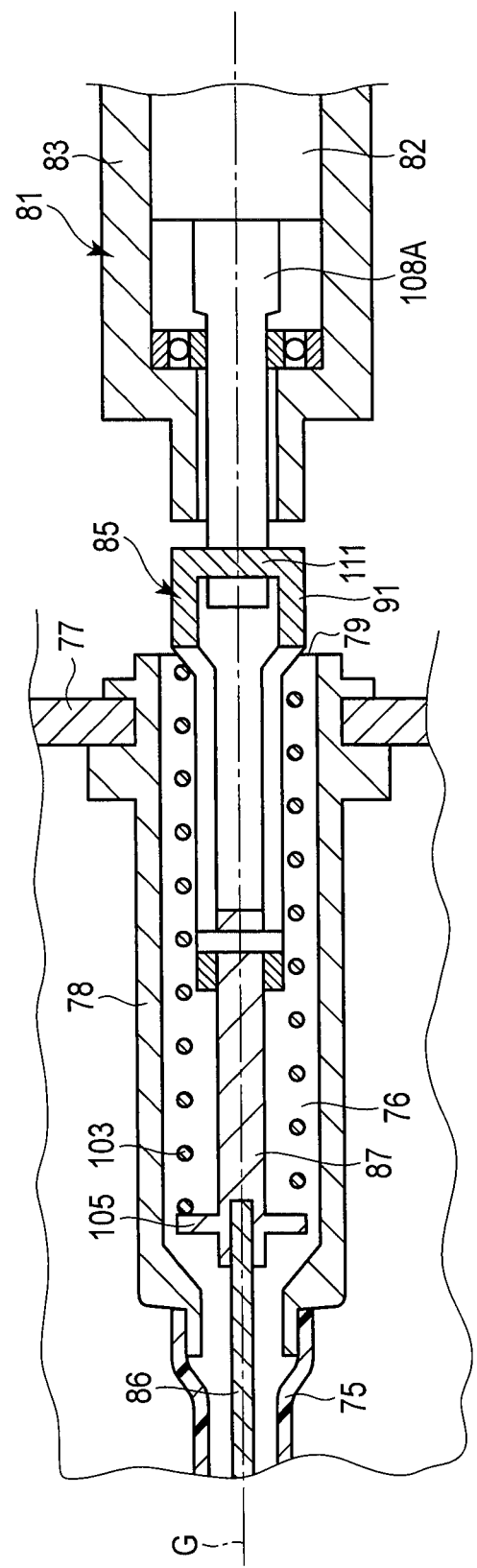
F I G. 9

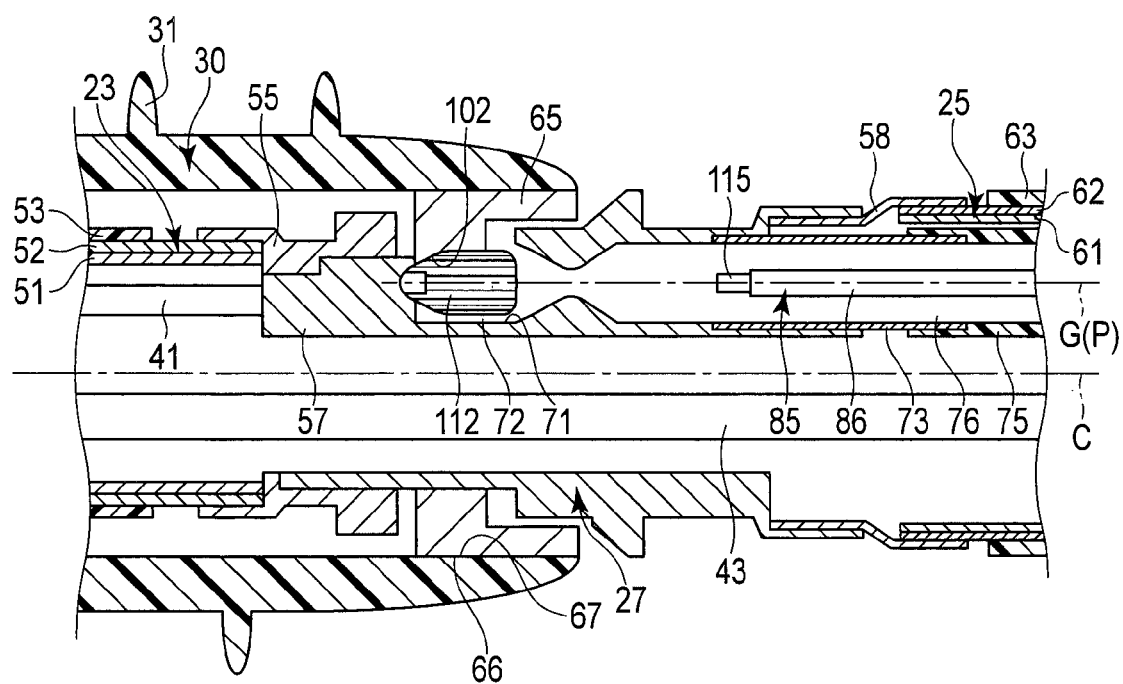
F I G. 10
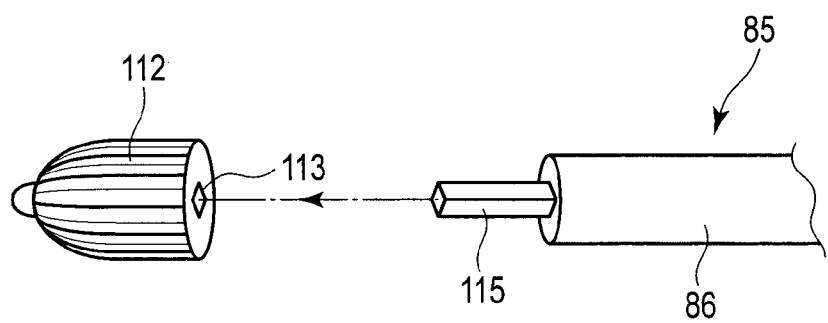
F I G. 11

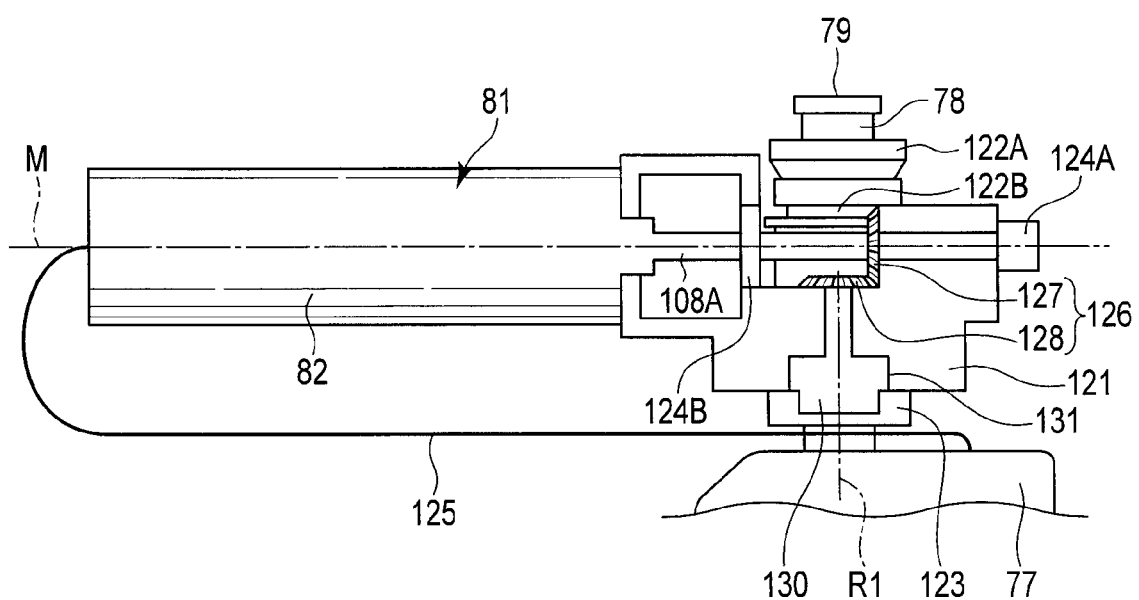
F I G. 14

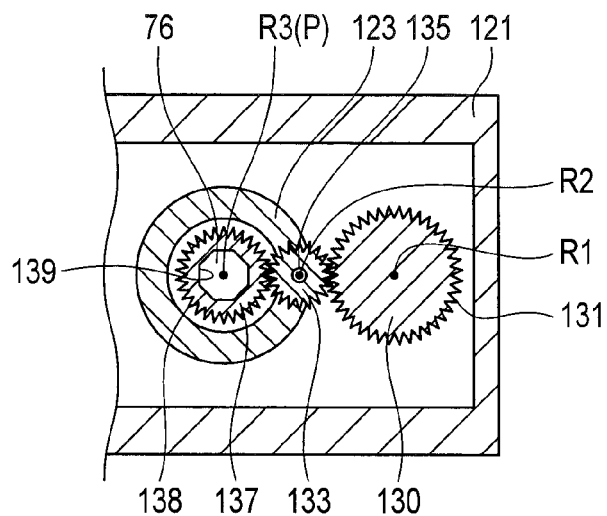
F I G. 16
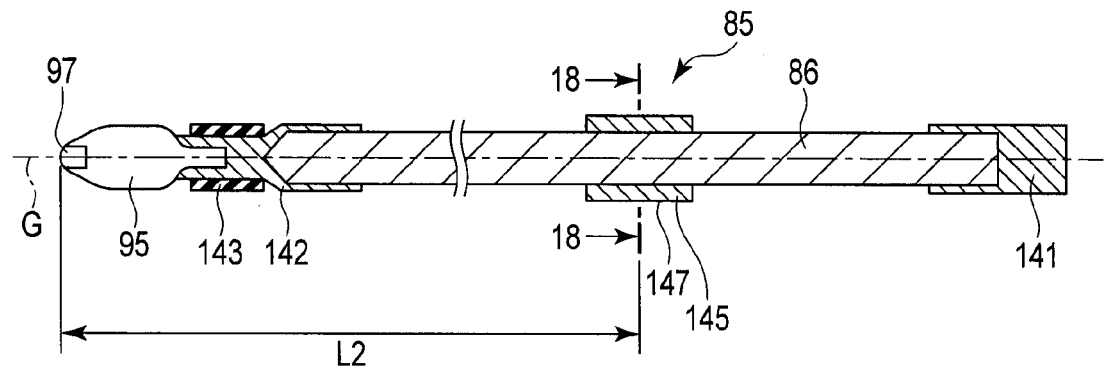
F I G. 17
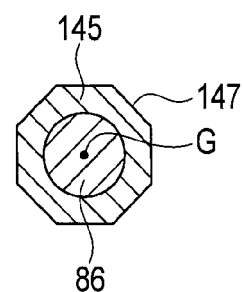
F I G. 18

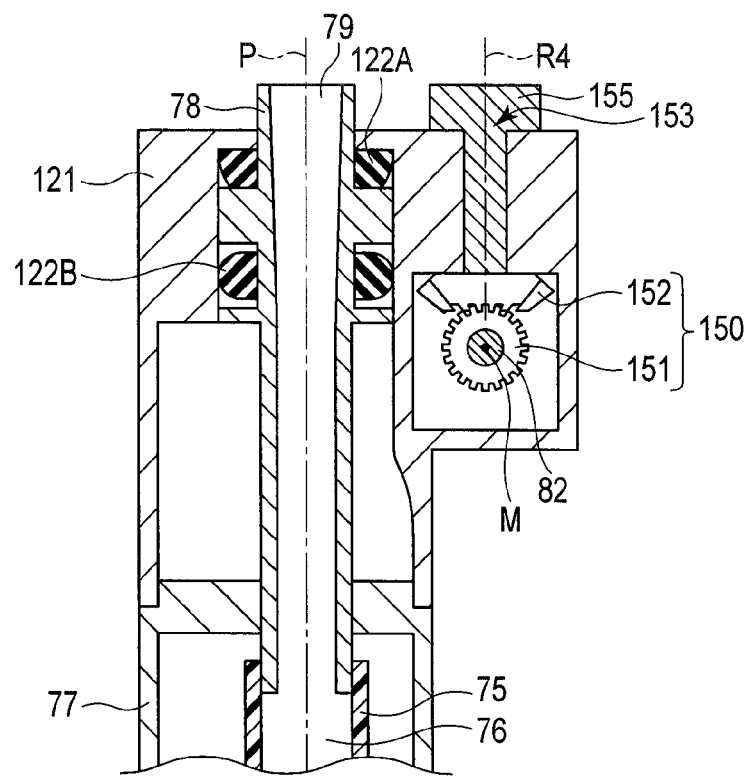
F I G. 21
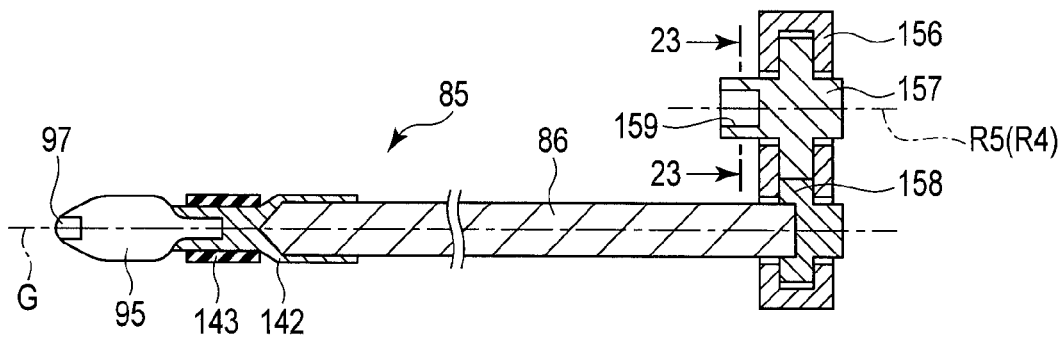
F I G. 22
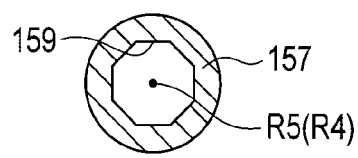
F I G. 23

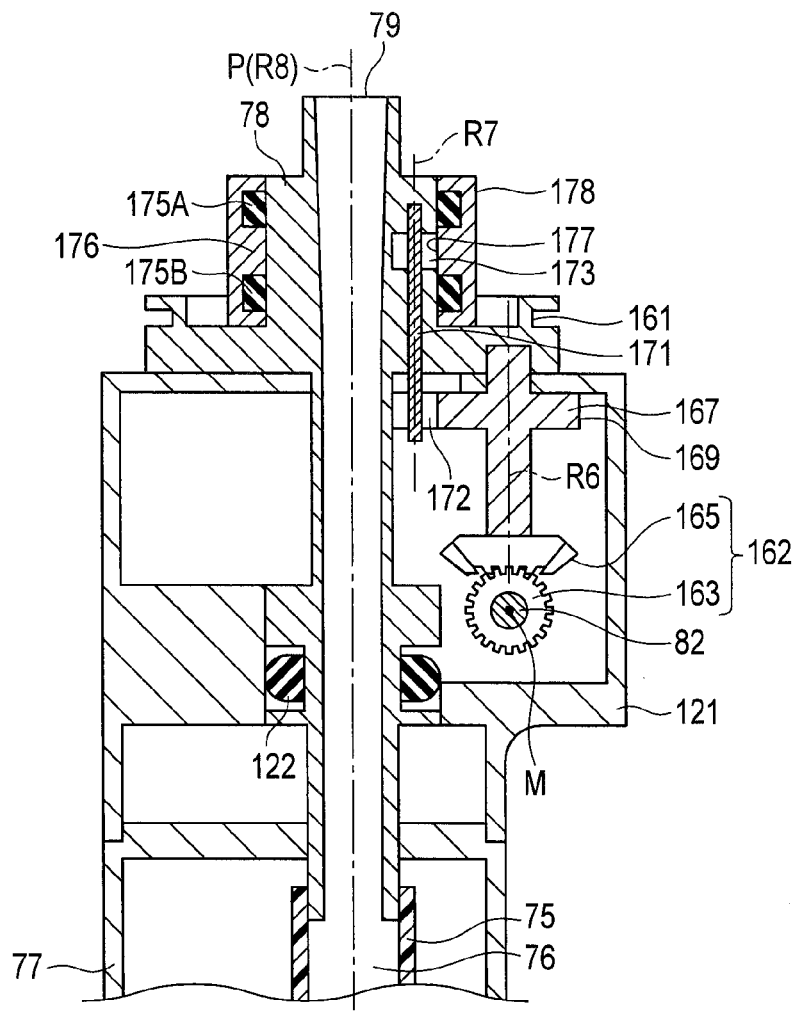
F I G. 27
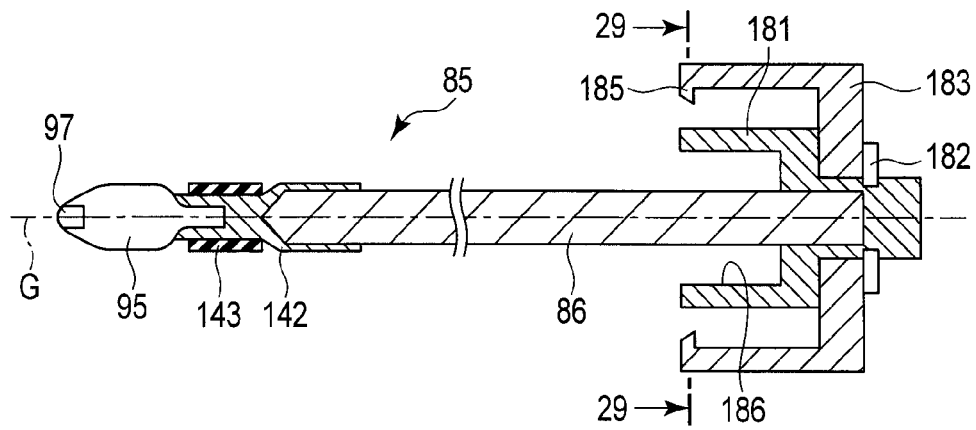
F I G. 28

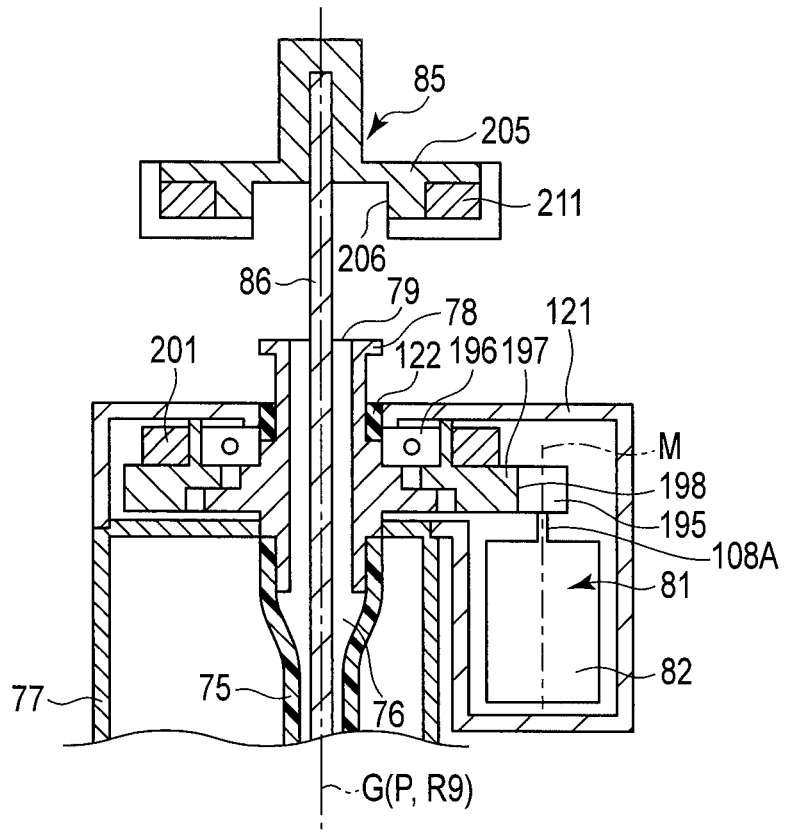
F I G. 31
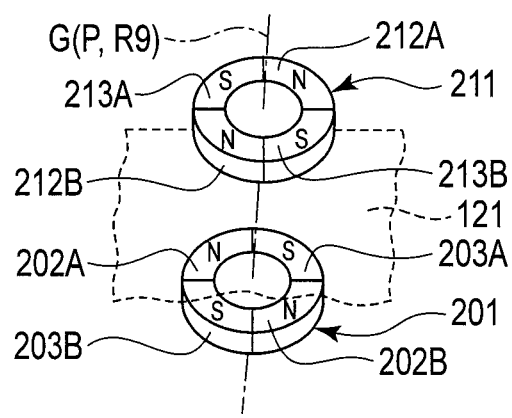
F I G. 32

DRIVING FORCE TRANSMITTING UNIT, INSERTION INSTRUMENT, ROTARY UNIT, INSERTION BODY ASSEMBLY, AND INSERTION DEVICE

CROSS-REFERENCE TO RELATED APPLICATIONS

This is a Continuation Application of PCT Application No. PCT/JP2013/074293, filed Sep. 9, 2013 and based upon and claiming the benefit of priority from prior Japanese Patent Application No. 2012-200983, filed Sep. 12, 2012, and prior Japanese Patent Application No. 2012-213062, filed Sep. 26, 2012, the entire contents of both of which are incorporated herein by reference.

BACKGROUND OF THE INVENTION

1. Field of the Invention

The present invention relates to a rotary unit attached, rotatably in directions around a longitudinal axis, to an insertion section extending along the longitudinal axis in an insertion instrument. The present invention also relates to an insertion instrument including an insertion section to which the rotary unit is attached, and an insertion body assembly provided in the insertion instrument. The present invention also relates to a driving force transmitting unit which extends through an inside of the insertion section and which is configured to transmit a rotation driving force to rotate the rotary unit. Moreover, the present invention relates to an insertion device including the insertion body assembly, the driving force transmitting unit, and the rotary unit.

2. Description of the Related Art

Jpn. Pat. Appln. KOKAI Publication No. 2005-288035 has disclosed a treatment apparatus which is an insertion device that can be inserted through a treatment tool channel of an endoscope. An insertion section extends in this treatment device along a longitudinal axis. A holding section is provided to a proximal direction side with respect to the insertion section. A spiral propulsion portion which serves as a rotary unit is attached to a distal portion of the insertion section rotatably relative to the insertion section in directions around the longitudinal axis. A channel extends through an inside of the holding section and through an inside of the insertion section along the longitudinal axis. A driving force transmitting unit extends through the channel. A flexible shaft which serves as a linear portion extends in the driving force transmitting unit. When the flexible shaft rotates around a drive axis (the longitudinal axis), a rotation driving force to rotate the spiral propulsion portion is transmitted to the spiral propulsion portion. The channel is open in an opening provided to the holding section. A proximal end of the flexible shaft is connected to a motor which serves as a driving source in a vicinity of the opening. When the motor is driven, the flexible shaft rotates around the drive axis, and the spiral propulsion portion rotates relative to the insertion section.

Jpn. Pat. Appln. KOKAI Publication No. 2007-185394 has disclosed an endoscope device as an insertion device. The endoscope device includes an insertion section provided along a longitudinal axis, and a rotary unit provided in a distal portion of the insertion section rotatably relative to the insertion section in directions around the longitudinal axis. A rotation gear is provided inside the insertion section. An inner peripheral gear portion which meshes with the rotation gear is provided in the rotary unit. When the rotation gear is actuated and rotated, a rotation driving force is transmitted to the rotary unit. As a result, the rotary unit rotates relative to the insertion section. A channel extends through an inside of the insertion section. A driving force transmitting unit connected to the rotation gear extends inside the channel. The driving force transmitting unit includes a line portion extending along a drive axis. A distal portion of the line portion is connected to the rotation gear. When the driving force transmitting unit rotates around the drive axis, the rotation driving force is transmitted to the rotation gear, and the rotation gear is actuated.

BRIEF SUMMARY OF THE INVENTION

According to one aspect of the invention, a driving force transmitting unit in an insertion device, the insertion device including an insertion section extending along a longitudinal axis, a rotary unit provided to an outer peripheral side of the insertion section rotatably relative to the insertion section in directions around the longitudinal axis, a base portion which is provided in the insertion section in a state that the rotary unit is attached rotatably in the directions around the longitudinal axis and which defines a cavity open to an outside and an inside of the insertion section, an actuation unit which is attached to the base portion to be located in the cavity and which is actuated in a state that the rotary unit is attached to the base portion, and thereby is configured to transmit a rotation driving force to rotate the rotary unit to the rotary unit, a holding section which is provided to a proximal direction side with respect to the insertion section and in which an insertion hole open to an outside of the holding section is formed, a driving source unit which is provided in the holding section or removably attached to the holding section, the driving source unit including a driving source which is driven so as to generate the rotation driving force, and a channel defining portion which defines a channel extending to the cavity of the base portion from the insertion hole of the holding section through an inside of the holding section and through an inside of the insertion section, the driving force transmitting unit being removably attached to the actuation unit in the cavity when inserted through the channel from the insertion hole, the driving force transmitting unit being configured to transmit the rotation driving force to the actuation unit by rotating around a driving axis when the driving force transmitting unit is attached to the actuation unit, the driving force transmitting unit including: a line portion which extends along the driving axis in the channel when the driving force transmitting unit is attached to the actuation unit, and which is insertable into the channel through the insertion hole and removable from the channel through the insertion hole; a distal connection portion which is provided in a distal portion of the line portion and which is connected to the actuation unit when the driving force transmitting unit is attached to the actuation unit; a driving force receiving portion which is provided in a proximal portion of the line portion or provided to the proximal direction side with respect to the line portion and which is located and set at a position to receive the rotation driving force from the driving source unit when the driving force transmitting unit is attached to the actuation unit; a slider portion which is attached to the proximal portion of the line portion and which is movable relative to the line portion along the driving axis; and an urging portion having a distal end connected to the line portion and a proximal end connected to the slider portion, the urging portion being configured to contract in response to a movement of the slider portion relative to the line portion toward a distal direction and thereby configured to apply an urging force toward the distal direction to the line portion and the distal connection portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a sectional view taken along the line IV-IV in FIG. 2;

FIG. 5 is a sectional view schematically showing the configuration of a unit insertion tube of a holding section in an unattached state in which a driving source unit is not attached to the unit insertion tube according to the first embodiment;

FIG. 9 is a sectional view schematically showing the configuration of the unit insertion tube of the holding section in the unattached state in which the driving source unit is not attached to the unit insertion tube according to the first modification;

FIG. 10 is a sectional view schematically showing the configuration of the second intermediary connection section of the insertion section when the driving force transmitting unit is not attached to the rotary cylindrical member according to a second modification;

FIG. 11 is a perspective view schematically showing the configuration in which an engaging end of the driving force transmitting unit is connected to a rotation gear of an actuation unit according to the second modification;

FIG. 14 is a schematic diagram showing the internal configuration of the motor casing of the holding section when seen from an arrow A1 direction in FIG. 13 according to the second embodiment;

FIG. 16 is a sectional view taken along the line 16-16 in FIG. 15;

FIG. 17 is a sectional view schematically showing the configuration of the driving force transmitting unit according to a second embodiment;

FIG. 18 is a sectional view taken along the line 18-18 in FIG. 17;

FIG. 21 is a sectional view schematically showing the internal configuration of the motor casing of the holding section in a section through the unit channel according to the third embodiment;

FIG. 22 is a sectional view schematically showing the configuration of the driving force transmitting unit according to the third embodiment;

FIG. 23 is a sectional view taken along the line 23-23 in FIG. 22;

FIG. 27 is a sectional view schematically showing the internal configuration of the motor casing of the holding section in a section through the unit channel according to the fourth embodiment;

FIG. 28 is a sectional view schematically showing the configuration of the driving force transmitting unit according to the fourth embodiment;

FIG. 31 is a sectional view schematically showing the configurations of the holding section and the driving force transmitting unit according to a fifth embodiment;

FIG. 32 is a schematic diagram showing the configurations of a driving source side magnet and an attachment side magnet according to the fifth embodiment;

DETAILED DESCRIPTION OF THE INVENTION

First Embodiment

Figure 1:
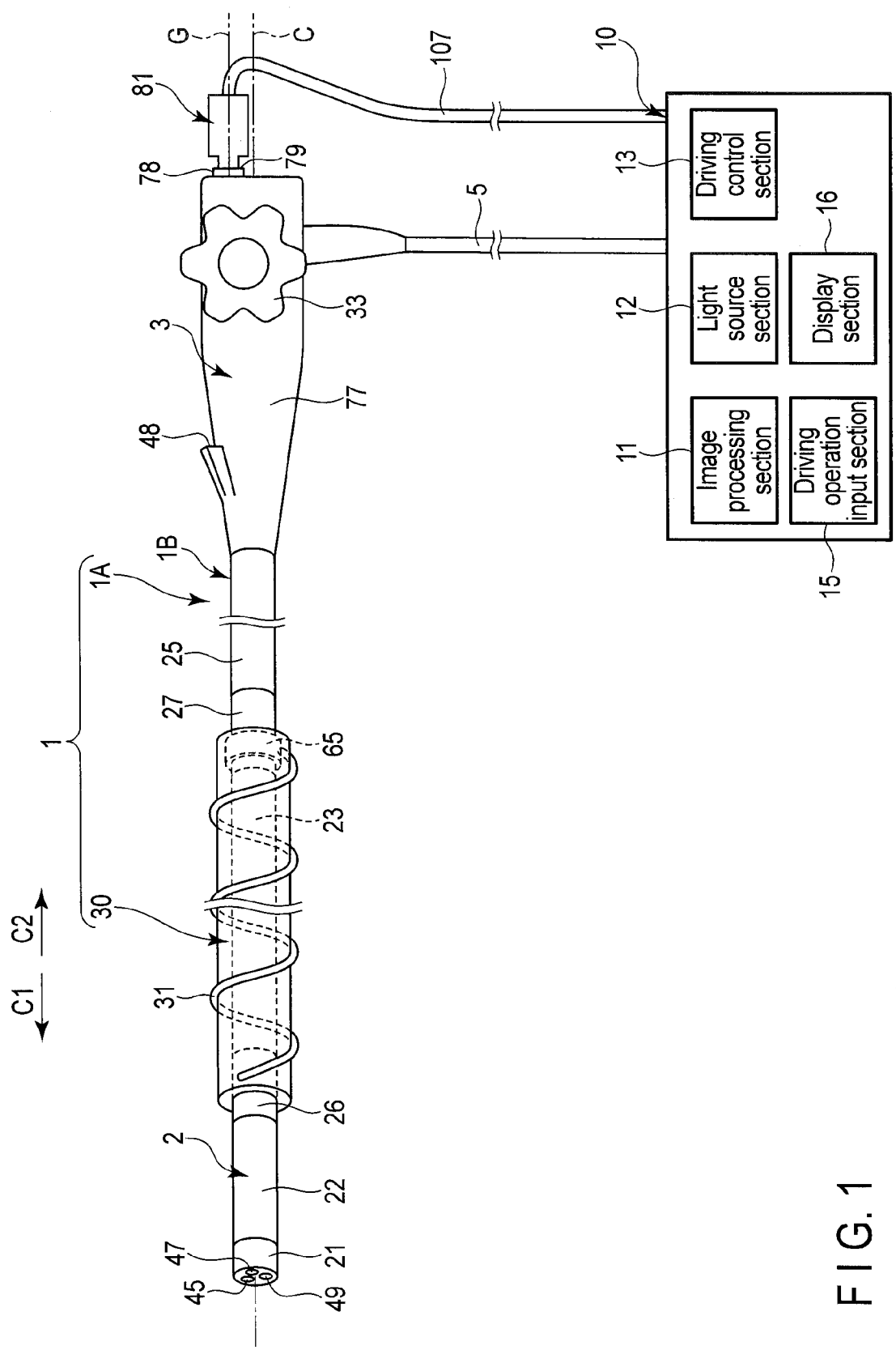
FIG. 1 is a schematic diagram showing an endoscope device according to a first embodiment.

A first embodiment of the present invention is described with reference to FIG. 1 to FIG. 7. FIG. 1 is a diagram showing an endoscope device 1 which is an insertion device according to the first embodiment. As shown in FIG. 1, the endoscope device 1 has a longitudinal axis C. One of directions parallel to the longitudinal axis C is a distal direction (direction of an arrow C1 in FIG. 1), and a direction opposite to the distal direction is a proximal direction (direction of an arrow C2 in FIG. 1). As shown in FIG. 1, the endoscope device 1 includes an endoscope 1A which is an insertion instrument, and a rotary unit 30 attached to the endoscope 1A. The endoscope 1A includes an insertion body assembly 1B serving as a main body, and a driving force transmitting unit 85 (not shown in FIG. 1) removably attached to the insertion body assembly 1B. The insertion body assembly 1B includes an insertion section (endoscopic insertion section) 2 extending along the longitudinal axis C from the proximal direction toward the distal direction, and a holding section (endoscopic holding section) 3 provided to the proximal direction side with respect to the insertion section 2. The insertion section 2 is inserted into a lumen during the use of the endoscope system 1. One end of a universal cable 5 is connected to the holding section 3. The other end of the universal cable 5 is connected to a peripheral unit 10. The peripheral unit 10 includes an image processing section 11, a light source section 12, a driving control section 13, a driving operation input section 15, and a display section 16.

The insertion section 2 includes a distal hard section 21, a bending section 22 provided to the proximal direction side with respect to the distal hard section 21, a first flexible tube section 23 provided to the proximal direction side with respect to the bending section 22, and a second flexible tube section 25 provided to the proximal direction side with respect to the first flexible tube section 23. The bending section 22 and the first flexible tube section 23 are connected by a first intermediary connection section 26. The first flexible tube section 23 and the second flexible tube section 25 are connected by a second intermediary connection section 27.

The rotary unit 30 is provided to an outer peripheral direction side of the insertion section 2. The insertion section 2 is inserted through the tube member 30. The rotary unit 30 extends along the longitudinal axis C between the first intermediary connection section 26 and the second intermediary connection section 27. The rotary unit 30 is rotatable relative to the insertion section 2 in directions around the longitudinal axis (around the longitudinal axis C). The rotary unit 30 includes a spiral fin portion 31 spirally extending around the longitudinal axis C.

Figure 2:
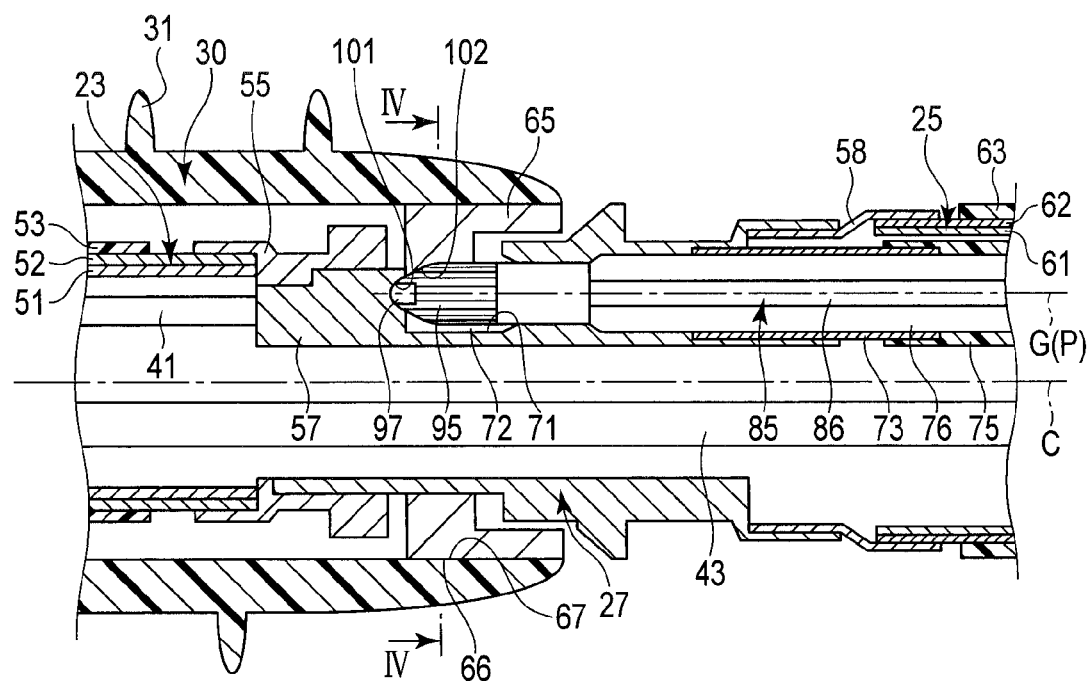
FIG. 2 is a sectional view schematically showing the configuration of a second intermediary connection section of an insertion section when a driving force transmitting unit is attached to a rotary cylindrical member according to the first embodiment.
Figure 3:
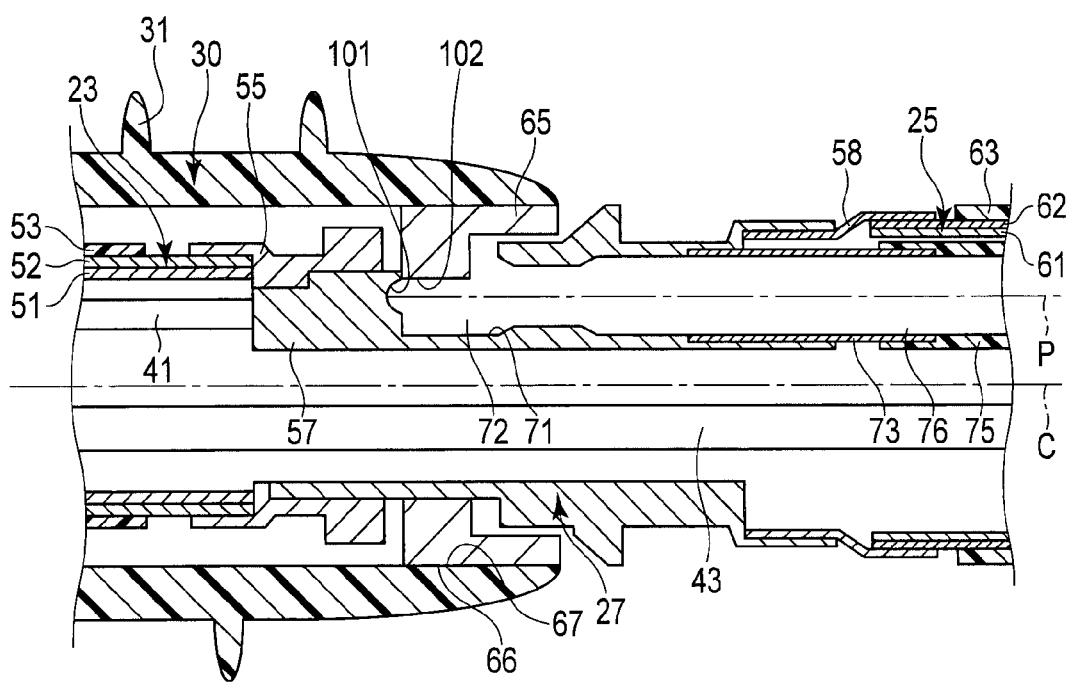
FIG. 3 is a sectional view schematically showing the configuration of the second intermediary connection section of the insertion section when the driving force transmitting unit is not attached to the rotary cylindrical member according to the first embodiment.

FIG. 2 and FIG. 3 are diagrams showing the configuration of the second intermediary connection section 27. FIG. 4 is a sectional view taken along the line IV-IV in FIG. 2. Here, FIG. 2 shows a state in which the driving force transmitting unit 85 is attached to the insertion body assembly 1B, and FIG. 3 shows a state in which the driving force transmitting unit 85 is not attached to the insertion body assembly 1B. As shown in FIG. 1, a bending operation knob 33 which serves as a bending operation input section to input a bending operation of the bending section 22 is provided on an outer surface of the holding section 3. As shown in FIG. 4, bending wires 35A and 35B extend through an inside of the insertion section 2 along the longitudinal axis C. The proximal ends of the bending wires 35A and 35B are connected to a pulley (not shown) coupled to the bending operation knob 33 inside the holding section 3. The distal ends of the bending wires 35A and 35B are connected to a distal portion of the bending section 22. In response to the bending operation in the bending operation knob 33, the bending wire 35A or the bending wire 35B is pulled, and the bending section 22 bends.

Each of the bending wires 35A and 35B is inserted through a corresponding coil 36A or 36B. The proximal ends of the coils 36A and 36B are fixed to the inner peripheral portion of the holding section 3. The distal ends of the coils 36A and 36B are connected to the inner peripheral portion of the first intermediary connection section 26. In the present embodiment, the two bending wires 35A and 35B are provided, and the bending section 22 is bendable in two directions. However, for example, four bending wires may be provided, and the bending section 22 may be bendable in four directions. Alternatively, no bending section 22 may be provided.

As shown in FIG. 2 to FIG. 4, an imaging cable 41, a light guide 42, and a treatment tool channel tube 43 extend through the inside of the insertion portion 2 along the longitudinal axis C. An image pickup element (not shown) for imaging a subject is provided inside the distal hard section 21 (the distal portion of the insertion section 2). The image pickup element is configured to image the subject through an observation window 45. The distal end of the imaging cable 41 is connected to the image pickup element. The imaging cable 41 extends through the inside of the insertion portion 2, the inside of the holding portion 3, and an inside of the universal cable 5, and has its proximal end connected to the image processing section 11 of the peripheral unit 10. Image processing of an obtained subject figure is performed by the image processing section 11, and an image of the subject is generated. The generated image of the subject is displayed on the display section 16.

The light guide 42 extends through the inside of the insertion section 2, the inside of the holding section 3, and the inside of the universal cable 5, and has its proximal end connected to the light source section 12 of the peripheral unit 10. Light emitted from the light source section 12 is guided by the light guide 42, and applied to the subject from an illumination window 47 in the distal portion (distal hard section 21) of the insertion section 2.

As shown in FIG. 1, a treatment tool insertion portion 48 into which a treatment tool such as a forceps is inserted is provided on the outer surface of the holding section 3. The treatment tool channel tube 43 has its proximal end connected to the treatment tool insertion portion 48 and extends through the inside of the insertion section 2 and the inside of the holding section 3. The treatment tool inserted from the treatment tool insertion portion 48 projects toward a distal direction from an opening 49 of the distal hard section 21 through an inside of the treatment tool channel tube 43. A treatment is then conducted by the treatment tool so that the treatment tool projects from the opening 49 of the distal hard section 21.

As shown in FIG. 2 and FIG. 3, a metallic first helical tube (first flex) 51 is provided in the first flexible tube section 23. The outer peripheral side of the first helical tube 51 is covered with a metallic first flexible mesh tube (first flexible braid) 52. The outer peripheral side of the first flexible mesh tube 52 is covered with a resin first flexible envelope 53. A proximal portion of the first helical tube 51 and a proximal portion of the first flexible mesh tube 52 are fitted in a distal portion of an intermediary member 55. The second intermediary connection section 27 includes a metallic base member 57. A proximal portion of the intermediary member 55 is fitted in the base member 57. In this way, the first flexible tube section 23 is coupled to, the second intermediary connection section 27.

A metallic second helical tube (second flex) 61 is provided in the second flexible tube section 25. The outer peripheral side of the second helical tube 61 is covered with a metallic second flexible mesh tube (second flexible braid) 62. The outer peripheral side of the second flexible mesh tube 62 is covered with a resin second flexible envelope 63. A distal portion of the second helical tube 61 and a distal portion of the second flexible mesh tube 62 are fitted in an intermediary member 58. The intermediary member 58 is fitted in the base member 57. In this way, the second flexible tube section 25 is coupled to, the second intermediary connection section 27.

A cavity 72 is defined in the base member 57 by a cavity defining portion 71. A rotary cylindrical body 65 is attached to the base member 57 so that the insertion section 2 is inserted therethrough. The rotary cylindrical body 65 is rotatable relative to the insertion section 2 in the directions around the longitudinal axis. The rotary unit 30 is located to the outer peripheral direction side of the rotary cylinder 65.

As shown in FIG. 4, the rotary cylindrical body 65 is provided with a polygonal outer peripheral portion 66 having a substantially hexagonal sectional shape in a section perpendicular to the longitudinal axis C. The rotary unit 30 is provided with a polygonal inner peripheral portion 67 in which a sectional shape in a section perpendicular to the longitudinal axis C passing through the rotary cylindrical body 65 is formed into a substantially hexagonal shape corresponding to the polygonal outer peripheral portion 66 of the rotary cylinder 65. Thus, the polygonal inner peripheral portion 67 of the rotary unit 30 is in close contact with the polygonal outer peripheral portion 66 of the rotary cylindrical body 65, and the rotary unit 30 is fixed to the outer peripheral side of the rotary cylindrical body 65.

As a result, the rotary unit 30 is rotatable relative to the insertion section 2 in the directions around the longitudinal axis together with the rotary cylinder 65. That is, the base member 57 serves as a base portion to which the rotary unit 30 is attached via the rotary cylindrical body 65 rotatably in the directions around the longitudinal axis. When the rotary cylindrical body 65 is actuated and rotated, the rotational driving force to rotate the rotary unit 30 is transmitted to the rotary unit 30. That is, the rotary cylindrical body 65 serves as an actuation unit which is actuated and thereby configured to transmit the rotation driving force to the rotary unit 30.

As shown in FIG. 2 to FIG. 4, a distal end of a unit channel tube 75 is connected to the base member 57 via a connection tube 73. A unit channel (channel) 76 is defined inside the unit channel tube 75. That is, the unit channel tube 75 serves as a channel defining portion which defines the unit channel (channel) 76. The distal end of the unit channel 76 is in communication with the cavity 72. The unit channel 76 has a channel axis P.

As shown in FIG. 1, the holding section 3 includes a holding casing 77, and a unit insertion tube 78 attached to the holding casing 77. A unit insertion hole (insertion hole) 79 is formed in the unit insertion tube 78. In the unit insertion hole 79, a driving source unit (driving force generating unit) 81 is removably attached to the unit insertion tube 78 (holding section 3).

Figure 6:
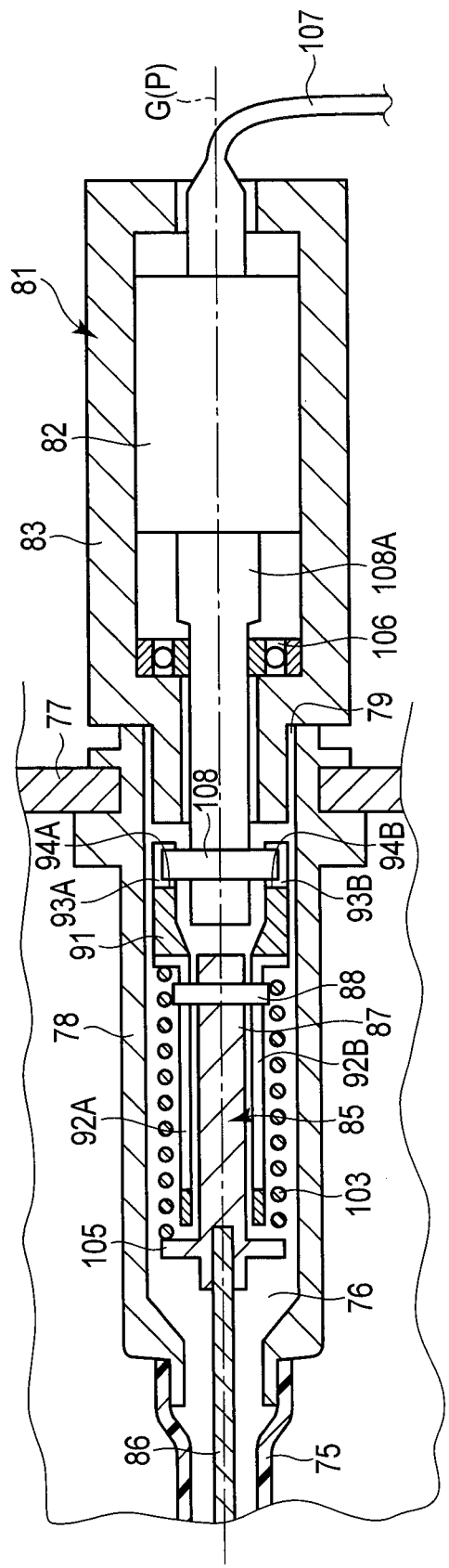
FIG. 6 is a sectional view schematically showing the configuration of the unit insertion tube of the holding section in an attached state in which the driving source unit is attached to the unit insertion tube according to the first embodiment.

FIG. 5 and FIG. 6 are diagrams showing the configuration of the unit insertion tube 78. Here, FIG. 5 shows an unattached state in which the driving source unit 81 is not attached to the unit insertion tube 78 of the holding section 3, and FIG. 6 shows an attached state in which the driving source unit 81 is attached to the unit insertion tube 78. As shown in FIG. 5 and FIG. 6, the proximal end of the unit channel tube 75 is connected to the unit insertion tube 78 inside the holding section 3. The unit channel 76 extends to the unit insertion hole 79 through an inside of the unit insertion tube 78. Therefore, the unit channel (channel) 76 extends to the cavity 72 of the base member 57 from the unit insertion hole (insertion hole) 79. That is, the unit channel 76 extends through the inside of the holding section 3 and through the inside of the insertion section 2.

The driving force transmitting unit (attachment unit) 85 can be inserted into the unit channel 76 from the unit insertion hole 79. That is, the driving force transmitting unit 85 is inserted into the inside of the holding section 3 and the inside of the insertion section 2 from the unit insertion hole 79. As shown in FIG. 2, FIG. 5, and FIG. 6, the driving force transmitting unit 85 has a driving axis G substantially parallel to the longitudinal axis C. The driving force transmitting unit 85 is inserted from the unit insertion hole 79 into the unit channel 76 extending through the inside of the insertion section 2 and through the inside of the holding section 3. When the driving force transmitting unit 85 is inserted in the unit channel 76, the driving force transmitting unit 85 is removably attached to the rotary cylinder 65 which serves as the actuation unit. The driving force transmitting unit 85 is removable from the unit channel 76 through the unit insertion hole 79. Here, FIG. 2 shows a state in which the driving force transmitting unit 85 is attached to the rotary cylindrical body 65, and FIG. 3 shows a state in which the driving force transmitting unit 85 is not attached to the rotary cylindrical body 65.

Figure 7:
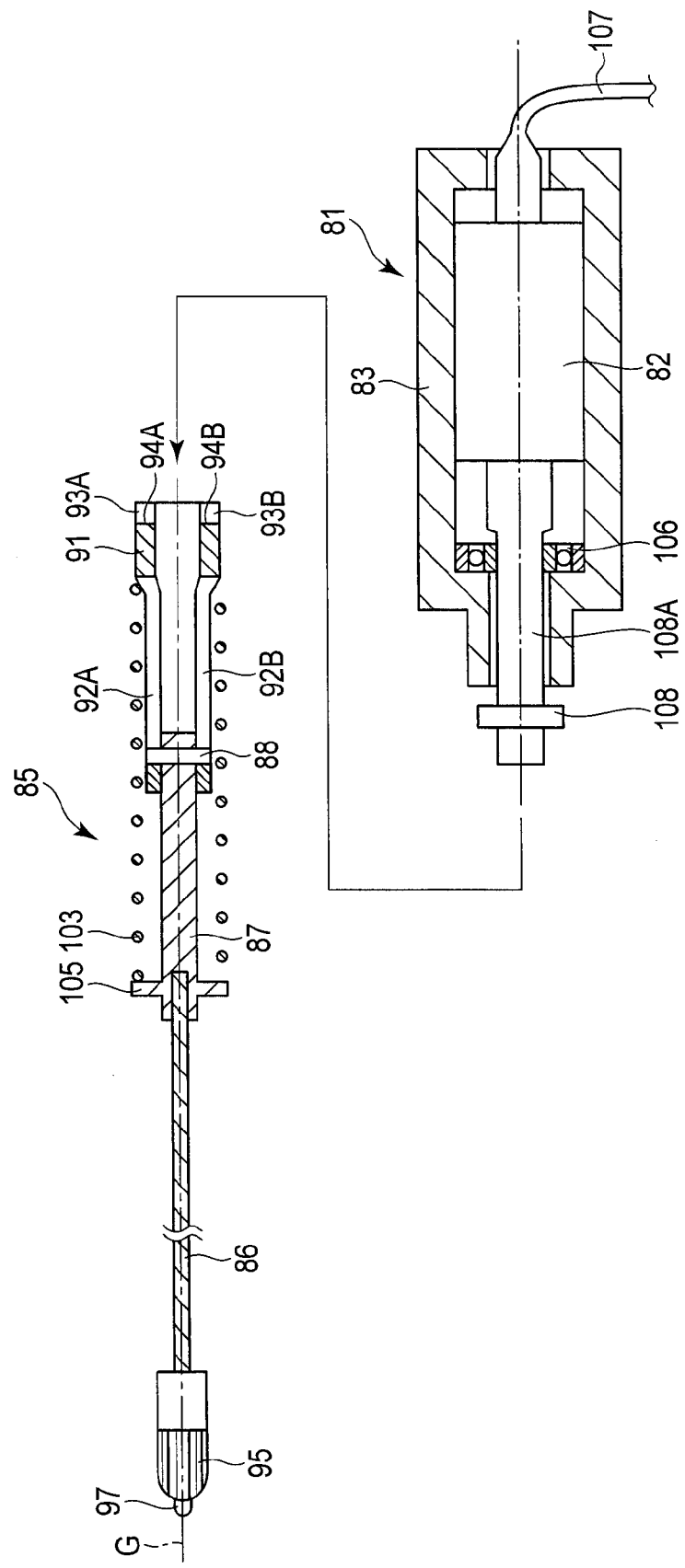
FIG. 7 is a sectional view schematically showing the configurations of the driving force transmitting unit and the driving source unit according to the first embodiment.

FIG. 7 is a diagram showing the configurations of the driving force transmitting unit 85 and the driving source unit 81. As shown in FIG. 7, the driving force transmitting unit 85 includes a drive shaft 86, and an intermediary member 87 to which a proximal end of the drive shaft 86 is connected. The drive shaft 86 and the intermediary member 87 serve as a line portion extending along the driving axis G. The drive shaft 86 and the intermediary member 87 which serve as the line portion are insertable into the unit channel 76 through the unit insertion hole 79, and removable from the unit channel 76 through the unit insertion hole 79. As shown in FIG. 2 and FIG. 6, when the driving force transmitting unit 85 is attached to the rotary cylindrical body 65, the drive shaft 86 and the intermediary member 87 extend along the unit channel 76 through the inside of the insertion section 2 and through the inside of the holding section 3.

A coupling member 88 is fixed to a proximal portion of the intermediary member 87. A cylindrical slider portion 91 is attached to the intermediary member 87 via the coupling member 88. Two through-holes 92A and 92B passing from an outside of the slider portion 91 to an inside are formed in the slider portion 91. The through-holes 92A and 92B are formed into long hole shapes along the driving axis G. When the coupling member 88 is inserted in the through-holes 92A and 92B, the slider portion 91 is attached to the intermediary member 87 (strand portion). Since the through-holes 92A and 92B are formed into the long hole shapes, the slider portion 91 is movable relative to the drive shaft 86 and the intermediary member 87 (line portion) along the driving axis G.

In the proximal portion of the slider portion 91, each of cutouts 93A and 93B passing from the outside of the slider portion 91 to the inside is defined by a corresponding cutout defining surface 94A or 94B. The cutouts 93A and 93B are formed along the driving axis G from the proximal end of the slider portion 91.

The distal end of the drive shaft 86 is connected to a rotation gear 95. That is, the driving force transmitting unit 85 includes the rotation gear 95 provided in the distal portion of the wire portion (the drive shaft 86 and the intermediary member 87). An engagement protrusion 97 protruding toward the distal direction is provided in the rotation gear 95. As shown in FIG. 2 and FIG. 4, when the driving force transmitting unit 85 is attached to the rotary cylindrical body 65, the rotation gear 95 is located in the cavity 72. An engagement slot 101 which is engageable with the engagement protrusion 97 of the rotation gear 95 is provided in the base member 57. When the driving force transmitting unit 85 is attached to the rotary cylindrical body 65, the engagement protrusion 97 of the rotation gear 95 is engaged with the engagement slot 101 of the base member 57.

An inner peripheral gear portion 102 is provided over the all-round of the rotary cylindrical body 65. When the driving force transmitting unit 85 is attached to the rotary cylindrical body 65, the inner peripheral gear portion 102 meshes with the rotation gear 95. When the rotation driving force to rotate the rotary unit 30 is transmitted, the driving force transmitting unit 85 rotates around the driving axis G. As a result, the rotation gear 95 rotates around the driving axis G, and the rotation driving force is transmitted to the rotary cylindrical body 65 which serves as the actuation unit via the inner peripheral gear portion 102. The rotary cylindrical body 65 then rotates relative to the insertion section 2 toward one of the directions around the longitudinal axis. As described above, the rotation gear 95 serves as a distal connection portion to be connected to the rotary cylindrical body 65 when the driving force transmitting unit 85 is attached to the rotary cylindrical body 65 which serves as the actuation unit. The rotation gear 95 is connected to the rotary cylindrical body 65 which serves as the actuation unit in the cavity 72.

As shown in FIG. 5 to FIG. 7, the driving force transmitting unit 85 includes an elastic member 103 which is an urging portion. A receiving portion 105 is provided in the distal portion of the intermediary member 87 (strand portion). The distal end of the elastic member 103 is connected to the receiving portion 105. The proximal end of the elastic member 103 is connected to the slider portion 91. The elastic member 103 is connected to the slider portion 91 at the position between the through-holes 92A and 92B and the cutouts 93A and 93B in directions parallel to the driving axis G.

As shown in FIG. 6 and FIG. 7, the driving source unit 81 includes a motor 82 which serves as a driving source, and a motor casing 83 which houses the motor 82 therein. The motor 82 is attached to the motor casing 83 via a bearing 106. As shown in FIG. 1, one end of a motor cable 107 is connected to the motor 82. The other end of the motor cable 107 is connected to the driving control section 13 of the peripheral unit 10. Electric power (electric current) is supplied to the motor 82 from the driving control section 13 by a driving operation in the driving operation input section 15. The motor 82 is driven by the supply of the electric power, and a motor shaft 108A rotates. When the motor 82 is driven, a rotation driving force to rotate the rotary unit 30 is generated.

As shown in FIG. 6 and FIG. 7, a connection member 108 is fixed to a distal portion of the motor shaft 108A of the motor 82. When the connection member 108 is engaged with the cutouts 93A and 93B of the slider portion 91, the motor 82 is removably connected to the proximal direction side of the slider portion 91. That is, the cutouts 93A and 93B serve as a driving source connection portion configured to removably connect the motor 82 which serves as the driving source to the proximal direction side of the slider portion 91.

When the connection member 108 is engaged with the cutouts 93A and 93B, the connection member 108 attached to the motor shaft 108A is in abutment with the cutout defining surfaces 94A and 94B. As a result, the rotation driving force can be transmitted to the cutout defining surfaces 94A and 94B of the slider portion 91 of the driving force transmitting unit 85 from the motor 82 of the driving source unit 81. That is, the cutout defining surfaces 94A and 94B serve as a driving force receiving portion configured to receive the rotation driving force from the motor 82. The cutout defining surfaces 94A and 94B are located in the slider portion 91, and provided to the proximal direction side with respect to the intermediary member 87 (line portion). When the driving force transmitting unit 85 is attached to the rotary cylindrical body 65 which serves as the actuation unit, the cutout defining surfaces 94A and 94B which serve as the driving force receiving portion are located and set at positions to receive the rotation driving force from the driving source unit 81. When the cutout defining surfaces 94A and 94B which serve as the driving force receiving portion are located and set at the positions to receive the rotation driving force, the motor 82 of the driving source unit 81 is removably connected to the cutout defining surfaces 94A and 94B.

As shown in FIG. 5, in the unattached state in which the driving source unit 81 is not attached to the unit insertion tube 78 of the holding section 3, the slider portion 91 of the driving force transmitting unit 85 protrudes to the outside of the holding section 3 from the unit insertion hole 79 of the unit insertion tube 78. Thus, in the unattached state, the cutouts 93A and 93B which serve as the driving source connection portion and the cutout defining surfaces 94A and 94B which serve as the driving force receiving portion are located outside the holding section 3. Therefore, the motor 82 which serves as the driving source is connected to the slider portion 91 outside the holding section 3. In the unattached state, the elastic member 103 extends between the intermediary member 87 (line portion) and the slider portion 91 in a reference state.

As shown in FIG. 6, when the motor casing 83 is engaged with the unit insertion tube 78, the attached state is set in which the driving source unit 81 is attached to the unit insertion tube 78. In the attached state, the motor 82 is connected to the slider portion 91. Thus, when the motor 82 is driven, the cutout defining surfaces 94A and 94B receive the rotation driving force generated in the motor 82, and the rotation driving force is transmitted to the driving force transmitting unit 85. As a result, the driving force transmitting unit 85 rotates around the driving axis G.

In the attached state, the slider portion 91 is pressed from the driving source unit 81 toward the distal direction. When the slider portion 91 is pressed, the slider portion 91 moves toward the distal direction from the unattached state. In response to the movement of the slider portion 91 toward the distal direction, the elastic member 103 contracts from the reference state. As a result, an urging force toward the distal direction is applied to the drive shaft 86, the intermediary member 87 (line portion), and the rotation gear 95 from the elastic member 103 which serves as the urging portion.

Now, the function and advantageous effects of the endoscope device 1 which is the insertion device according to the present embodiment are described. When the endoscope system 1 is used, the driving force transmitting unit (attachment unit) 85 is inserted into the unit channel 76 from the unit insertion hole 79 while the rotary unit 30 and the rotary cylindrical body 65 which serves as the actuation unit are attached to the base member (base portion) 57 of the insertion section 2. The driving force transmitting unit 85 is then inserted through the unit channel 76, and the engagement protrusion 97 of the rotation gear 95 is engaged with the engagement slot 101 of the base member 57. The rotation gear 95 is brought into mesh with the inner peripheral gear portion 102 of the rotary cylindrical body 65. As a result, the rotation gear 95 which serves as the distal connection portion is connected to the rotary cylindrical body 65 which serves as the actuation unit, and the driving force transmitting unit 85 is attached to the rotary cylindrical body 65.

When the connection member 108 is engaged with the cutouts 93A and 93B of the slider portion 91, the motor 82 which is the driving source is connected to the proximal direction side of the slider portion 91. In the unattached state in which the driving source unit (driving force generating unit) 81 is not attached to the unit insertion tube 78 of the holding section 3, the slider portion 91 of the driving force transmitting unit 85 protrudes to the outside of the holding section 3 from the unit insertion hole 79 of the unit insertion tube 78. In the unattached state, the cutouts 93A and 93B which serve as the driving source connection portion and the cutout defining surfaces 94A and 94B which serve as the driving force receiving portion are located outside the holding section 3. When the cutouts 93A and 93B and the cutout defining surfaces 94A and 94B are located outside the holding section 3, the motor 82 can be easily connected to the slider portion 91.

The motor casing 83 is then engaged with the unit insertion tube 78, and the driving source unit 81 is attached to the unit insertion tube 78. As a result, the attached state is set in which the driving source unit 81 is attached to the unit insertion tube 78. The insertion section 2 and the rotary unit 30 are then inserted into the lumen, and the electric power is supplied to the motor 82 from the driving control section 13 by a driving operation in the driving operation input section 15. As a result, the motor 82 is driven, and the rotation driving force to rotate the rotary unit 30 relative to the insertion section 2 in one of the directions around the longitudinal axis is generated.

When the motor 82 is driven, the motor shaft 108A rotates, and the cutout defining surfaces 94A and 94B of the driving force transmitting unit 85 receive the rotation driving force. As a result, the rotation driving force is transmitted to the driving force transmitting unit 85, and the driving force transmitting unit 85 rotates around the driving axis G (channel axis P). As a result, the rotation gear 95 rotates around the driving axis G, and the rotation driving force is transmitted to the rotary cylindrical body 65 which serves as the actuation unit via the inner peripheral gear portion 102. The rotary cylinder 65 is then actuated, and rotates relative to the insertion section 2 in one of the directions around the longitudinal axis. As a result, the rotation driving force is transmitted to the rotary unit 30 from the rotary cylindrical body 65, and the rotary unit 30 rotates in one of the directions around the longitudinal axis together with the rotary cylindrical body 65.

When the rotary unit 30 is rotated in one direction around the longitudinal axis while a press force is being applied to the spiral fin portion 31 from the lumen wall toward an inner peripheral direction, a propulsive force toward the distal direction is applied to the rotary unit 30 and the insertion section 2. As a result, mobility, that is, insertability of the insertion section 2 in the distal direction parallel to the longitudinal axis C in the lumen improves. When the rotary unit 30 is rotated in the other direction around the longitudinal axis while the press force is being applied to the spiral fin portion 31 from the lumen wall toward the inner peripheral direction, a propulsive force toward the proximal direction is applied to the rotary unit 30 and the insertion section 2. As a result, mobility, that is, removability of the insertion section 2 in the proximal direction parallel to the longitudinal axis C in the lumen improves.

In the attached state, the slider portion 91 is pressed from the driving source unit 81 toward the distal direction. When the slider portion 91 is pressed, the slider portion 91 moves toward the distal direction from the unattached state. In response to the movement of the slider portion 91 in the distal direction, the elastic member 103 contracts from the reference state. As a result, the urging force toward the distal direction is applied to the drive shaft 86, the intermediary member 87 (line portion), and the rotation gear 95 from the elastic member 103 which serves as the urging portion.

The second flexible tube section 25 is flexible, and deformed by the application of an external force. Thus, when the second flexible tube section 25 is deformed while the driving force transmitting unit 85 is attached to the rotary cylindrical body 65, the drive shaft 86 and the intermediary member 87 (line portion) are deformed in response to the deformation of the second flexible tube section 25. Here, in the present embodiment, the urging force toward the distal direction is applied to the drive shaft 86, the intermediary member 87 (strand portion), and the rotation gear 95 from the elastic member 103. Thus, even when the drive shaft 86 and the intermediary member 87 are deformed, the rotation gear 95 is properly engaged with the inner peripheral gear portion 102 of the rotary cylindrical body 65. That is, even when the drive shaft 86 and the intermediary member 87 are deformed, the rotation gear 95 which serves as the distal connection portion is properly connected to the rotary cylindrical body 65 which serves as the actuation unit. Therefore, even when the second flexible tube section 25 is deformed, the rotation driving force can be properly transmitted to the rotary unit 30 from the driving force transmitting unit 85 via the rotary cylindrical body 65, and the rotary unit 30 can be properly rotated.

After the use of the endoscope device 1, the driving source unit 81 is separated from the unit insertion tube 78. As a result, the unattached state is set in which the driving source unit 81 is not attached to the unit insertion tube 78. The motor 82 is then removed from the cutouts 93A and 93B of the slider portion 91. In the unattached state, the cutouts 93A and 93B which serve as the driving source connection portion and the cutout defining surfaces 94A and 94B which serve as the driving force receiving portion are located outside the holding section 3. When the cutouts 93A and 93B and the cutout defining surfaces 94A and 94B are located outside the holding section 3, the motor 82 can be easily removed from the slider portion 91. The driving force transmitting unit 85 is then removed from the unit channel 76 through the unit insertion hole 79.

After the use of the endoscope device 1, the insertion body assembly 1B (the insertion section 2 and the holding section 3) is cleaned by an endoscope cleaner while the driving force transmitting unit 85 is removed from the unit channel 76. Since the unit channel 76 is cleaned while the driving force transmitting unit 85 is removed in the cleaning of the insertion body assembly 1B, cleaning performance for the unit channel 76 can be ensured.

The driving source unit 81 having the large-sized motor 82 is attachable to and detachable from the slider portion 91 of the driving force transmitting unit 85. Thus, the driving force transmitting unit 85 removed from the unit channel 76 is cleaned while the driving source unit 81 is detached. That is, the driving force transmitting unit 85 having the drive shaft 86 is cleaned separately from the driving source unit 81. Therefore, cleaning performance for the driving force transmitting unit 85 can be ensured.

Modification of First Embodiment

Figure 8:
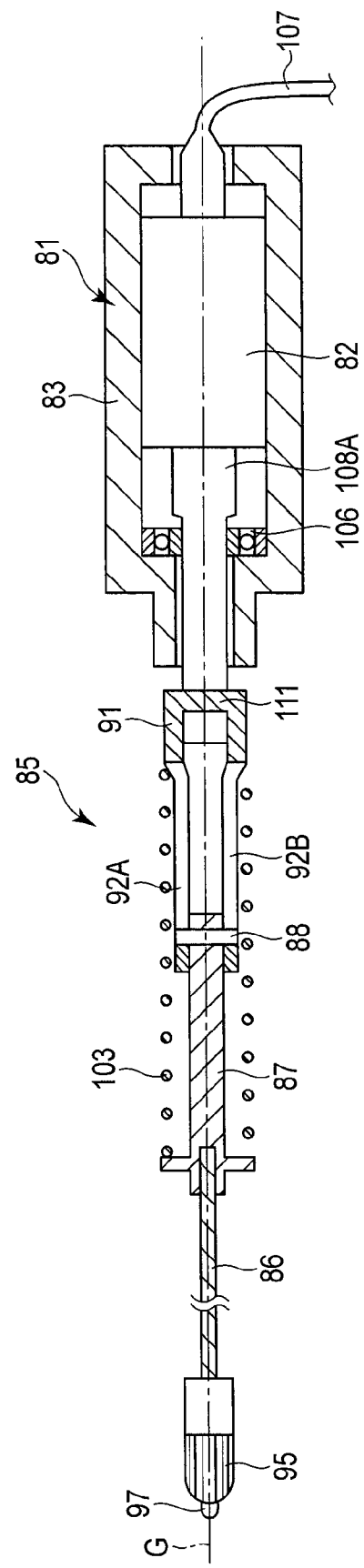
FIG. 8 is a sectional view schematically showing the configuration of the driving force transmitting unit according to a first modification.

Although the motor 82 is attachable to and detachable from the slider portion 91 of the driving force transmitting unit 85 in the first embodiment, this is not a limitation. For example, as in a first modification shown in FIG. 8 and FIG. 9, the driving source unit (driving force generating unit) 81 may be configured to be unremovable from the slider portion 91. In the present modification, the cutouts 93A and 93B are not provided in the slider portion 91, and a connection portion 111 is provided integrally with the slider portion 91. The slider portion 91 is fixed to the motor 82 in the connection portion 111. That is, the connection portion 111 serves as the driving source connection portion configured to connect the motor 82 which is the driving source to the proximal direction side of the slider portion 91. The connection portion 111 also serves as the driving force receiving portion configured to receive the rotation driving force from the motor 82. The connection portion 111 is located in the slider portion 91, and provided to the proximal direction side with respect to the intermediary member 87 (strand portion). When the driving force transmitting unit 85 is attached to the rotary cylindrical body 65 which serves as the actuation unit, the connection portion which serves as the driving force receiving portion is located and set at the position to receive the rotation driving force from the driving source unit 81.

In the present modification, the driving source unit 81 cannot be removed from the slider portion 91, so that the driving source unit 81 including the motor 82 is provided integrally with the driving force transmitting unit 85. That is, the driving source unit 81 which generates the rotation driving force is provided to be inseparable from the driving force transmitting unit 85.

In the present modification as well, in the unattached state in which the driving source unit 81 is not attached to the unit insertion tube 78 of the holding section 3, the slider portion 91 of the driving force transmitting unit 85 protrudes to the outside of the holding section 3 from the unit insertion hole 79 of the unit insertion tube 78. In the unattached state, the connection portion 111 which serves as the driving source connection portion and the driving force receiving portion are located outside the holding section 3.

In the present modification as well, in the attached state in which the driving source unit 81 is attached to the unit insertion tube 78, the slider portion 91 is pressed from the driving source unit 81 toward the distal direction. When the slider portion 91 is pressed, the slider portion 91 moves toward the distal direction from the unattached state. In response to the movement of the slider portion 91 in the distal direction, the elastic member 103 contracts from the reference state. As a result, the urging force toward the distal direction is applied to the drive shaft 86, the intermediary member 87 (line portion), and the rotation gear 95 from the elastic member 103 which serves as the urging portion.

Although the driving force transmitting unit 85 includes the rotation gear 95 in the first embodiment, this is not a limitation. For example, as in a second modification shown in FIG. 10 and FIG. 11, no rotation gear 95 may be provided in the driving force transmitting unit 85. In the present modification, a rotation gear 112 is provided in the cavity 72 defined by the base member 57. The rotation gear 112 is engaged with the inner peripheral gear portion 102 of the rotary cylindrical body 65.

The rotation gear 112 is rotatable around the driving axis G. When the rotation gear 112 rotates, the rotary cylindrical body 65 rotates relative to the insertion section 2 toward on of the directions around the longitudinal axis. As a result, the rotary unit 30 rotates relative to the insertion section 2 in one of the directions around the longitudinal axis together with the rotary cylindrical body 65. That is, in the present modification, the rotary cylindrical body 65 and the rotation gear 112 serve as the actuation unit configured to transmit the rotation driving force to the rotary unit 30 when actuated.

The rotation gear 112 is provided with an engagement slot 113 having a substantially square section perpendicular to the driving axis G. An engaging end 115 having a substantially square section perpendicular to the driving axis G is provided in the distal portion of the drive shaft 86 (line portion). The sectional shape of the engaging end 115 perpendicular to the driving axis G corresponds to the sectional shape of the engagement slot 113 perpendicular to the driving axis G.

When the rotary unit 30 is rotated, the driving force transmitting unit 85 is inserted into the unit channel 76 from the unit insertion hole 79, and the engaging end 115 of the drive shaft 86 is engaged with the engagement slot 113 of the rotation gear 112. As a result, the driving force transmitting unit 85 is attached to the rotation gear 112 and the rotary cylindrical body 65 which serve as the actuation unit. That is, the engaging end 115 serves as the distal connection portion to be connected to the rotation gear 112 (actuation unit). When the engaging end 115 is connected to the rotation gear 112, the rotation driving force can be transmitted to the rotation gear 112 and the rotary cylindrical body 65 from the driving force transmitting unit 85. The engaging end 115 is connected to the rotation gear 112 which serves as the actuation unit in the cavity 72.

In the first embodiment and its modification, the driving force transmitting unit 85 includes the line portion (86, 87) extending along the driving axis G (channel axis P) through the inside of the insertion portion 2 and through the inside of the holding portion 3 when the driving force transmitting unit 85 is attached to the actuation unit (65; 65, 112), and a distal connection portion (95; 115) which is provided in the distal portion of the line portion (86, 87) and which is connected to the actuation unit (65; 65, 112) when the driving force transmitting unit 85 is attached to the actuation unit (65; 65, 112). The driving force transmitting unit 85 includes the slider portion 91 which is attached to the proximal portion of the line portion (86, 87) and which is movable relative to the line portion (86, 87) along the driving axis G, and the urging portion (103) having the distal end connected to the line portion (86, 87) and the proximal end connected to the slider portion 91. When the urging portion (103) contracts in response to the movement of the slider portion 91 relative to the line portion (86, 87) toward the distal direction, the urging force toward the distal direction is applied to the line portion (86, 87) and the distal connection portion (95; 115) from the urging portion (103). The slider portion 91 is provided with the driving force receiving portion (94A, 94B; 111) which is located and set at the position to receive the rotation driving force from the driving source unit 81 when the driving force transmitting unit 85 is attached to the actuation unit (65; 65, 112).

Second Embodiment

Now, a second embodiment of the present invention is described with reference to FIG. 12 to FIG. 18. In the second embodiment, the configuration according to the first embodiment is modified as below. The same parts as those in the first embodiment are provided with the same reference numerals, and are not described.

Figure 12:
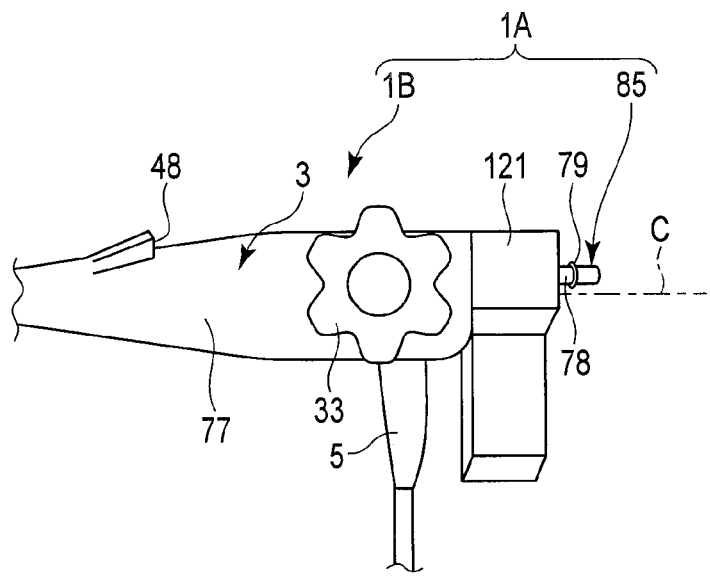
FIG. 12 is a schematic diagram showing the configuration of the holding section according to a second embodiment.

FIG. 12 is a diagram showing the configuration of the holding section 3 of the insertion body assembly 1B according to the present embodiment. As shown in FIG. 12, the holding section 3 is provided with a motor casing 121 attached to a holding casing 77, in addition to the holding casing 77 similar to that in the first embodiment. The unit insertion tube 78 is attached to the motor casing 121. As in the first embodiment, the unit insertion hole (insertion hole) 79 is formed in the unit insertion tube 78.

Figure 13:
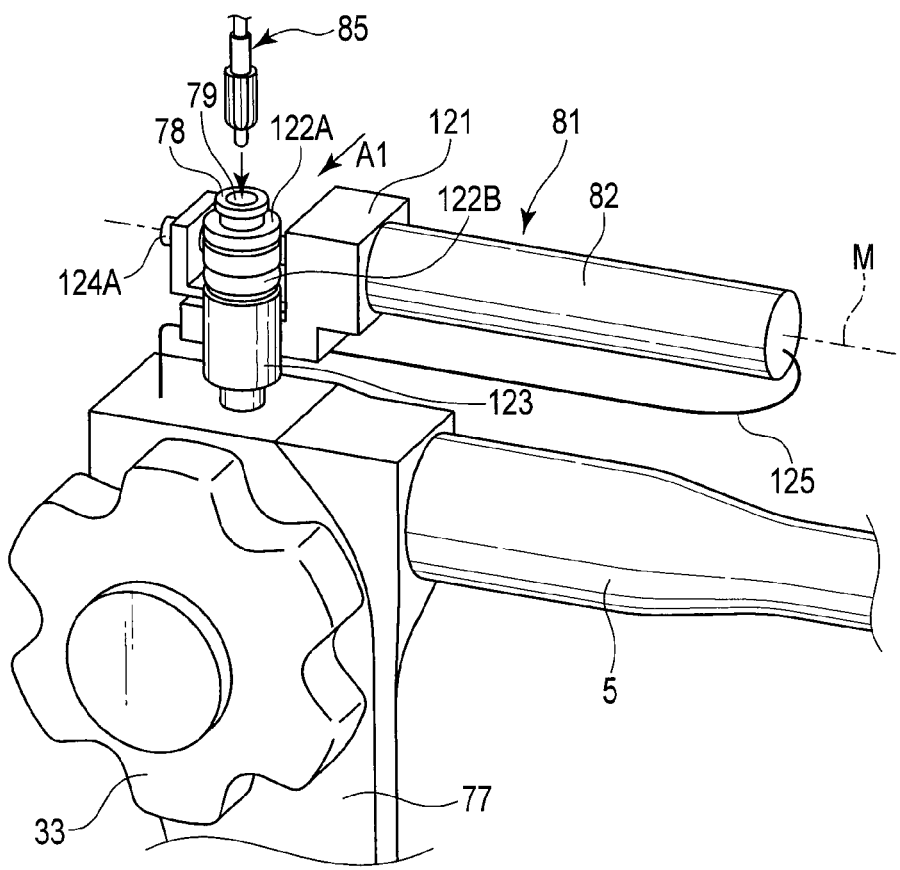
FIG. 13 is a perspective view schematically showing the internal configuration of a motor casing of the holding section according to the second embodiment.
Figure 15:
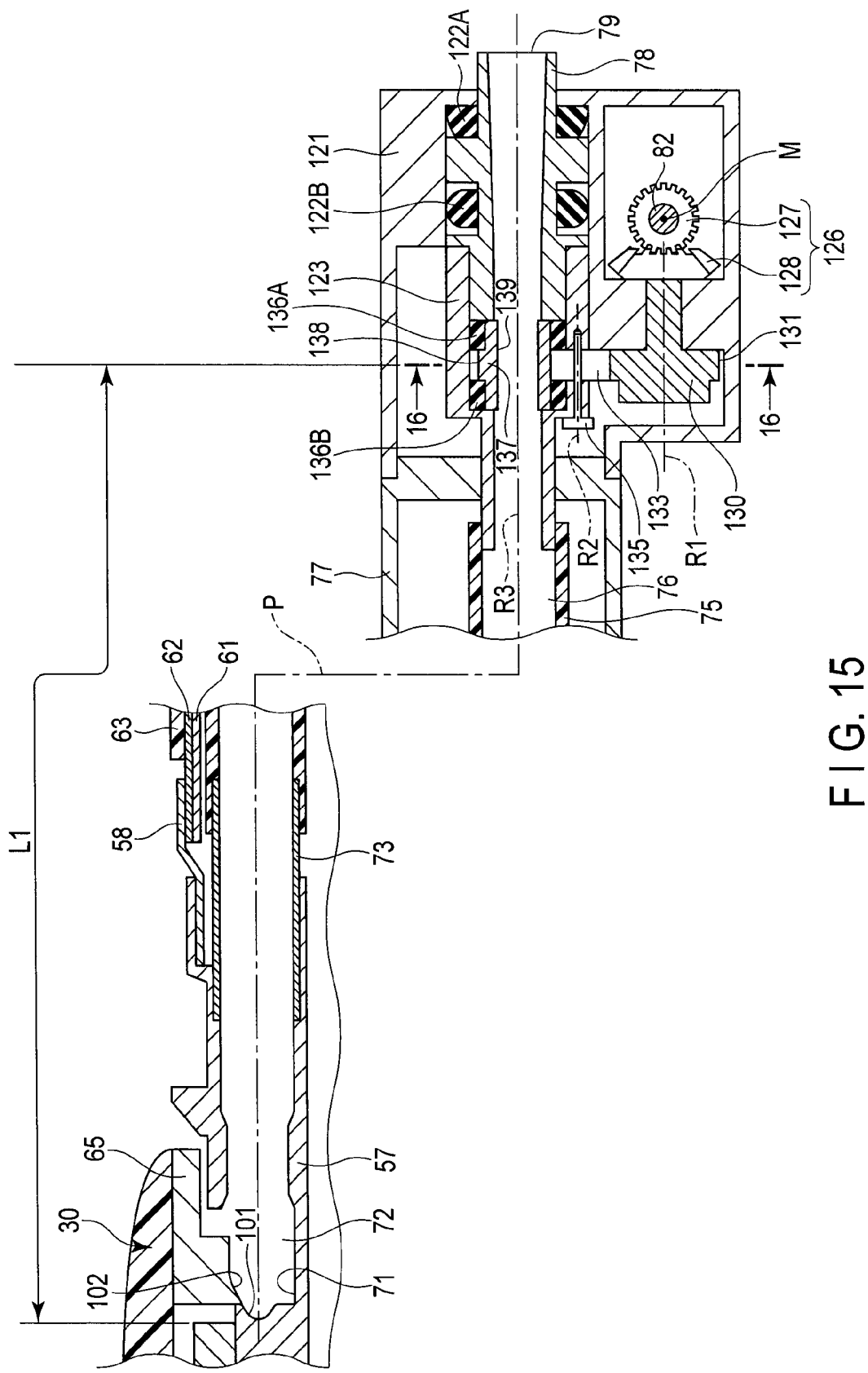
FIG. 15 is a sectional view schematically showing the configurations of the insertion section and the holding section in a section through a unit channel according to the second embodiment.

FIG. 13 and FIG. 14 are diagrams showing the internal configuration of the motor casing 121 of the holding section 3. Here, FIG. 13 is a perspective view, and FIG. 14 is a view of FIG. 13 when seen from an arrow A1 direction. FIG. 15 is a diagram showing the configuration of the insertion section 2 and the configuration of the holding section 3 in a section through the unit channel 76. As shown in FIG. 13 to FIG. 15, the unit insertion tube 78 is fixed to the motor casing 121 via seal rings 122A and 122B. A connection tube 123 is fixed to the unit insertion tube 78. The connection tube 123 extends from the inside of the motor casing 121 to the inside of the holding casing 77. Inside the holding casing 77, the proximal end of the unit channel tube 75 is connected to the connection tube 123.

The unit channel 76 is open to the outside of the holding section 3 in the unit insertion hole 79 and extends through an inside of the connection tube 123 and through an inside of the unit insertion tube 78. That is, the unit channel (channel) 76 extends to the cavity 72 of the base member (base portion) 57 from the unit insertion hole 79 through the inside of the holding section 3 and through the inside of the insertion section 2. In the base member 57, the unit channel 76 is in communication with the cavity (gear location cavity) 72.

The driving source unit 81 is provided inside the motor casing 121. The motor 82 which is the driving source of the driving source unit 81 is attached to the motor casing 121 via bearings 124A and 124B. One end of an electric wiring line 125 is connected to the motor 82. The other end of the electric wiring line 125 is connected to the driving control section 13 (see FIG. 1) of the peripheral unit 10 through the inside of the universal cable 5. An electric power (electric current) is supplied to the motor 82 from the driving control section 13 by a driving operation in the driving operation input section 15 (see FIG. 1). The motor 82 is driven by the supply of the electric power, and a motor shaft 108A rotates around a motor axis M. When the motor 82 is driven, the rotation driving force to rotate the rotary unit 30 is generated.

As shown in FIG. 14 and FIG. 15, a bevel wheel 126 is attached to the motor shaft 108A of the motor 82. The bevel wheel 126 includes a wheel 127 attached to the motor shaft 108A, and a wheel 128 which meshes with the wheel 127. When the motor 82 is driven, the wheel 127 rotates around the motor axis M together with the motor shaft 108A. The wheel 128 rotates around a rotation axis R1 perpendicular to the motor axis M in response to the rotation of the wheel 127.

FIG. 16 is a sectional view taken along the line 16-16 in FIG. 15. As shown in FIG. 14 to FIG. 16, a shaft member 130 is attached to the motor casing 121. The wheel 128 of the bevel wheel 126 is fixed to the shaft member 130. Therefore, in response to the rotation of the wheel 127, the shaft member 130 rotates around the rotation axis R1 together with the wheel 128. A gear portion 131 is provided on an outer peripheral portion of the shaft member 130. An intermediate gear 133 is attached to the motor casing 121 via a coupling pin 135. The gear portion 131 of the shaft member 130 meshes with the intermediate gear 133. In response to the rotation of the shaft member 130, the intermediate gear 133 rotates around a rotation axis R2 parallel to the rotation axis R1.

A tubular actuation member 137 is attached to the connection tube 123 via seal rings 136A and 136B. A gear portion 138 which meshes with the intermediate gear 133 is provided on an outer peripheral portion of the actuation member 137. In response to the rotation of the intermediate gear 133, the actuation member 137 rotates around a rotation axis (transmission rotation axis) R3 parallel to the rotation axis R2. Here, the unit channel 76 passes through an inside of the actuation member 137, and the rotation axis R3 of the actuation member 137 is coaxial with the channel axis P of the unit channel 76. The actuation member 137 includes a driving source side engagement surface 139 having a substantially octagonal section perpendicular to the rotation axis R3.

As described above, when the motor 82 which is the driving source is driven, the generated rotation driving force is transmitted to the actuation member 137 which serves as a driving source side actuation portion by the bevel wheel 126, the shaft member 130, and the intermediate gear 133. That is, the bevel wheel 126, the shaft member 130, and the intermediate gear 133 serve as a driving source side transmission portion configured to transmit the rotation driving force to the actuation member 137 which serves as the driving source side actuation portion from the motor 82 of the driving source unit 81. When the rotation driving force is transmitted, the actuation member 137 is actuated, and rotates around the rotation axis (transmission rotation axis) R3. That is, the actuation member 137 is a driving source side rotation portion which is actuated so as to rotate around the rotation axis (transmission rotation axis) R3.

In the present embodiment as well as in the first embodiment, the driving force transmitting unit (attachment unit) 85 is removably attached to the insertion body assembly 1B (the insertion section 2 and the holding section 3). The driving force transmitting unit 85 is insertable into the unit channel (channel) 76 from the unit insertion hole (insertion hole) 79, and removable from the unit channel 76 through the unit insertion hole 79.

FIG. 17 is a diagram showing the configuration of the driving force transmitting unit 85. As shown in FIG. 17, the drive shaft 86 which serves as the line portion extending along the driving axis G is provided in the driving force transmitting unit 85 according to the present embodiment, as in the first embodiment. The proximal end of the drive shaft 86 is connected to a columnar member 141. The distal end of the drive shaft 86 is connected to the rotation gear 95 via an intermediary member 142. A support ring 143 made of an elastic material is provided on the outer peripheral portion of the intermediary member 142. The drive shaft 86 and the rotation gear 95 are supported by the support ring 143 rotatably around the driving axis G. In the present embodiment as well, the engagement protrusion 97 protruding toward the distal direction is provided in the rotation gear 95.

In the present embodiment as well, the engagement protrusion 97 of the rotation gear 95 engages with the engagement slot 101 of the base member (base portion) 57 of the insertion section 2. The columnar member 141 of the driving force transmitting unit 85 engages with the unit insertion tube 78. The engagement protrusion 97 of the rotation gear 95 engages with the engagement slot 101 of the base member 57, and the columnar member 141 engages with the unit insertion tube 78, so that the driving force transmitting unit 85 is attached to the insertion section 2 and the holding section 3. That is, the driving force transmitting unit 85 is attached to the insertion section 2 and the holding section 3 while being inserted through the unit channel (channel) 76.

When the driving force transmitting unit 85 is attached to the insertion body assembly 1B, the drive shaft 86 which serves as the line portion extends through the unit channel 76, and the channel axis P of the unit channel 76 is coaxial with the driving axis G of the driving force transmitting unit 85. Therefore, when the driving force transmitting unit 85 is attached to the insertion section 2 and the holding section 3, the rotation axis (transmission rotation axis) R3 of the actuation member 137 is coaxial with the driving axis G of the driving force transmitting unit 85.

FIG. 18 is a sectional view taken along the line 18-18 in FIG. 17. As shown in FIG. 17 and FIG. 18, a cylindrical member 145 is fixed to an outer peripheral portion of the proximal portion of the drive shaft 86 which serves as the line portion. The drive shaft 86 is inserted through the cylindrical member 145. The cylindrical member 145 includes an attachment side engagement surface 147 having a substantially octagonal section perpendicular to the driving axis G. The shape of the attachment side engagement surface 147 of the cylindrical member 145 in the section perpendicular to the driving axis G corresponds to the shape of the driving source side engagement surface 139 of the actuation member 137 in the section perpendicular to the rotation axis R3.

When the driving force transmitting unit 85 is attached to the insertion section 2 and the holding section 3, the rotation axis (transmission rotation axis) R3 of the actuation member 137 is coaxial with the driving axis G of the driving force transmitting unit 85 (the drive shaft 86). An axially parallel dimension (first axially parallel dimension) L1 from the engagement slot 101 to the actuation member 137 along the channel axis P is substantially the same as an axially parallel dimension (second axially parallel dimension) L2 from the engagement protrusion 97 to the cylindrical member 145 along the driving axis G. Thus, when the driving force transmitting unit 85 is attached to the insertion section 2 and the holding section 3, the attachment side engagement surface 147 of the cylindrical member 145 engages with the driving source side engagement surface 139 of the actuation member 137. That is, the driving source side engagement surface 139 of the actuation member 137 serves as a driving source side connection portion. The attachment side engagement surface 147 of the cylindrical member 145 serves as an attachment side connection portion to be connected to the driving source side connection portion (139) when the driving force transmitting unit 85 is attached to the insertion section 2 and the holding section 3. In the present embodiment, the attachment side connection portion (147) is connected to the driving source side connection portion (139) inside the unit channel 76.

When the driving source side engagement surface 139 of the actuation member 137 is engaged with the attachment side engagement surface 147 of the cylindrical member 145, the rotation driving force can be transmitted to the attachment side engagement surface 147 of the driving force transmitting unit 85 from the driving source side engagement surface 139 of the driving source unit 81. That is, the attachment side engagement surface 147 serves as the driving force receiving portion configured to receive the rotation driving force from the driving source unit 81. The driving source side engagement surface 139 is provided at the proximal portion of the drive shaft 86 (line portion). When the driving force transmitting unit 85 is attached to the insertion body assembly 1B, the attachment side engagement surface 147 which serves as the driving force receiving portion is located and set at the position to receive the rotation driving force from the driving source unit 81.

When the driving force transmitting unit 85 is attached to the insertion section 2 and the holding section 3, the cylindrical member 145 receives the rotation driving force from the actuation member 137 which serves as the driving source side actuation portion in response to the rotation of the actuation member 137. As a result, the cylindrical member 145 rotates around the rotation axis R3 together with the actuation member 137. That is, the cylindrical member 145 is an attachment side actuation portion which receives the rotation driving force from the driving source side actuation portion (137) and is actuated by the actuation of the driving source side actuation portion (137) when the driving force transmitting unit 85 is attached to the insertion section 2 and the holding section 3. The cylindrical member 145 is also an attachment side rotation portion which rotates around the rotation axis (transmission rotation axis) R3 by being actuated when the driving force transmitting unit 85 is attached to the insertion section 2 and the holding section 3. The driving force receiving portion (147) is provided in the attachment side rotation portion (145).

When the cylindrical member 145 rotates around the rotation axis R3, the rotation driving force is transmitted to the drive shaft 86 from the cylindrical member 145. As a result, the drive shaft 86 which serves as the line portion rotates around the driving axis G. That is, the cylindrical member 145 is an attachment side transmission portion which is configured to transmit the rotation driving force to the strand portion (86) and rotates the line portion (86) around the driving axis G in response to the actuation of the attachment side rotation portion (145) when the attachment unit 85 is attached to the insertion section 2 and the holding section 3. When the drive shaft 86 rotates, the rotation gear 95 rotates around the driving axis G.

In the present embodiment as well as in the first embodiment, the rotary cylindrical body 65 is attached as the actuation unit to the base member 57. The inner peripheral gear portion 102 which meshes with the rotation gear 95 is provided on the inner peripheral portion of the rotary cylinder 65. In the present embodiment as well, the rotation gear 95 serves as the distal connection portion to be connected to the rotary cylindrical body 65 when the driving force transmitting unit 85 is attached to the rotary cylindrical body 65 which serves as the actuation unit. Thus, when the rotation gear 95 rotates around the driving axis G, the rotary cylindrical body 65 which serves as the actuation unit is actuated, and the rotary cylindrical body 65 rotates toward one of the directions around the longitudinal axis. When the rotary cylinder 65 rotates, the rotary unit 30 rotates relative to the insertion section 2 in one of the directions around the longitudinal axis. That is, when the rotation gear 95 rotates, the rotation driving force is transmitted to the rotary unit 30 via the rotary cylindrical body 65 which serves as the actuation unit from the driving force transmitting unit 85.

Now, the function and advantageous effects of the endoscope device 1 which is the insertion device according to the present embodiment are described. When the endoscope device 1 is used, the driving force transmitting unit 85 is inserted into the unit channel 76 from the unit insertion hole 79 while the rotary cylindrical body 65 and the rotary unit 30 are attached to the base member (base portion) 57 of the insertion section 2. The driving force transmitting unit 85 is then inserted through the unit channel 76, and the rotation gear 95 is thereby connected to the rotary cylindrical body 65 which serves as the actuation unit. As a result, the driving force transmitting unit 85 is attached to the insertion section 2 and the holding section 3, and also attached to the rotary cylindrical body 65.

When the rotation gear 95 of the driving force transmitting unit 85 is connected to the rotary cylindrical body 65, the attachment side engagement surface 147 of the cylindrical member 145 is engaged with the driving source side engagement surface 139 of the actuation member 137, and the attachment side engagement surface (attachment side connection portion) 147 is connected to the driving source side engagement surface (driving source side connection portion) 139.

The insertion section 2 and the rotary unit 30 are then inserted into the lumen. When the insertion section 2 is inserted in the lumen, an electric power is supplied to the motor 82 from the driving control section 13 by a driving operation in the driving operation input section 15, and the motor 82 is driven. As a result, the rotation driving force to rotate the rotary unit 30 relative to the insertion section 2 in one of the directions around the longitudinal axis is generated. When the motor shaft 108A of the motor 86 rotates around the motor axis M, the rotation driving force is transmitted from the motor 82 to the actuation member 137 which serves as the driving source side actuation portion by the bevel wheel 126, the shaft member 130, and the intermediate gear 133 which serve as the driving source side transmission portion. As a result, the actuation member 137 is actuated, and the actuation member 137 rotates around the rotation axis (transmission rotation axis) R3.

Here, the attachment side engagement surface 147 of the cylindrical member 145 is connected to the driving source side engagement surface 139 of the actuation member 137, so that when the actuation member 137 is actuated, the attachment side engagement surface 147 which serves as the driving force receiving portion of the cylindrical member 145 receives the rotation driving force from the actuation member 137. As a result, the cylindrical member 145 is actuated, and the cylindrical member 145 rotates around the rotation axis R3. When the cylindrical member 145 rotates, the drive shaft 86 which serves as the line portion rotates around the driving axis G (channel axis P), and the rotation gear 95 rotates around the driving axis G. As a result, the rotary cylindrical body 65 and the rotary unit 30 rotate in one of the directions around the longitudinal axis.

After the use of the endoscope device 1, the driving force transmitting unit 85 is detached from the insertion section 2 and the holding section 3, and the driving force transmitting unit 85 is detached from the rotary cylindrical body 65. The driving force transmitting unit 85 is then removed from the unit channel 76 through the unit insertion hole 79.

After the use of the endoscope device 1, the driving source unit 81 including the motor 82 which is the driving source is cleaned while being attached to the holding section 3. In this instance, the motor 82 is cleaned by the endoscope cleaner together with the insertion section 2 and the holding section 3. In the endoscope cleaner, the unit channel 76 is cleaned while the driving force transmitting unit 85 is removed. The driving force transmitting unit 85 is cleaned separately from the insertion section 2, the holding section 3, and the motor 82. As described above, the unit channel 76 is cleaned while the driving force transmitting unit 85 is removed, so that cleaning performance for the unit channel 76 can be ensured. The large-sized driving source unit 81 (motor 82) is cleaned together with the insertion section 2 and the holding section 3. That is, the drive shaft 86 which serves as the wire portion does not need to be cleaned together with the driving source unit 81. Therefore, a cleaning performance for the driving force transmitting unit 85 having the drive shaft 86 can be ensured.

When the driving force transmitting unit 85 is attached to the insertion section 2 and the holding section 3, the attachment side engagement surface (attachment side connection portion) 147 is connected to the driving source side engagement surface (driving source side connection portion) 139. That is, when the driving force transmitting unit 85 is inserted through the unit channel 76, the rotation driving force generated in the motor 82 can be transmitted to the drive shaft 86 which serves as the line portion. Therefore, even when the motor 82 which is the driving source is provided in the holding section 3, the driving force transmitting unit 85 having the drive shaft 86 can be easily attached to the insertion section 2 and the holding section 3.

The rotation axis R3 of the actuation member 137 provided with the driving source side engagement surface (driving source side connection portion) 139 and the cylindrical member 145 provided with the attachment side engagement surface (attachment side connection portion) 147 is coaxial with the driving axis G of the drive shaft 86 when the driving force transmitting unit 85 is attached to the rotary cylindrical body 65. The rotation axis R3 is coaxial with the driving axis G (channel axis P) of the drive shaft 86 when the driving force transmitting unit 85 is connected to the rotary cylindrical body 65, so that the configuration of the driving force transmitting unit 85 can be simpler.

Third Embodiment

Now, a third embodiment of the present invention is described with reference to FIG. 19 to FIG. 23. In the third embodiment, the configuration according to the second embodiment is modified as below. The same parts as those in the second embodiment are provided with the same reference numerals, and are not described.

Figure 19:
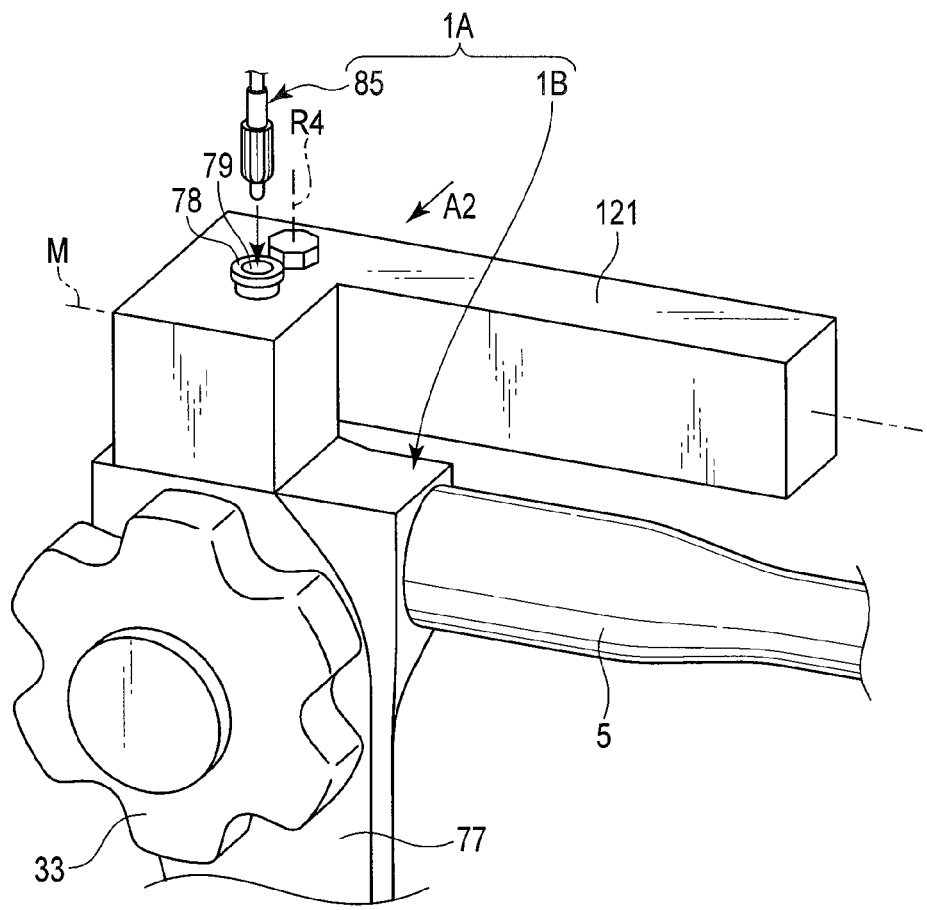
FIG. 19 is a perspective view schematically showing the configuration of the holding section according to a third embodiment.
Figure 20:
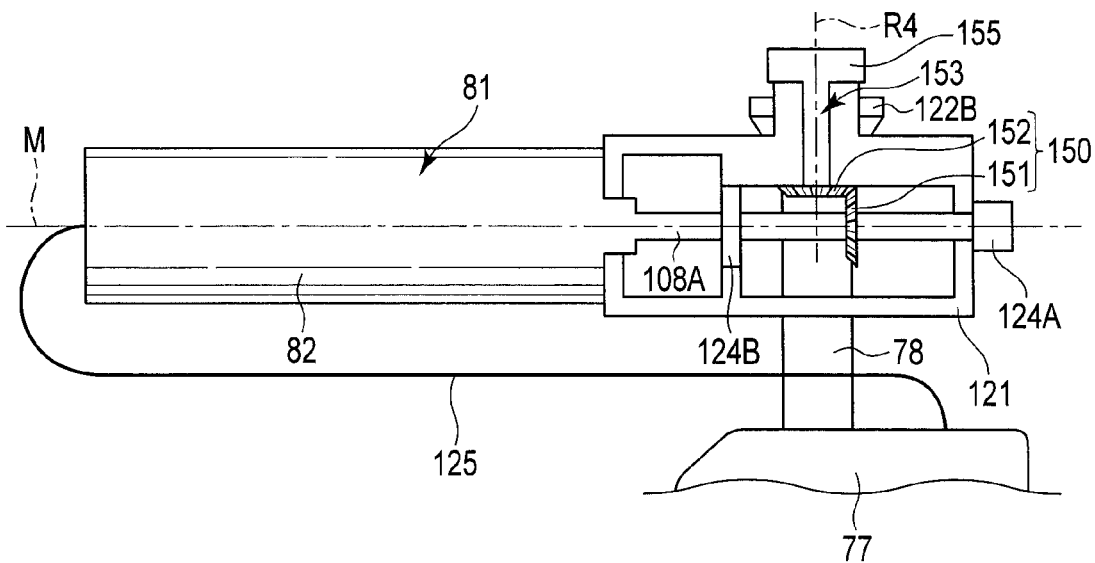
FIG. 20 is a schematic diagram showing the internal configuration of the motor casing of the holding section when seen from an arrow A2 direction in FIG. 19 according to the third embodiment.

FIG. 19 is a diagram showing the configuration of the holding section 3 of the insertion body assembly 1B according to the present embodiment. FIG. 20 and FIG. 21 are diagrams showing the internal configuration of the motor casing 121 of the holding section 3. Here, FIG. 20 is a diagram showing the inside of the motor casing 121 when seen from the direction of an arrow A2 in FIG. 19, and FIG. 21 is a diagram showing a section through the unit channel 76. As shown in FIG. 20 and FIG. 21, the unit insertion tube 78 is fixed to the motor casing 121 via the seal rings 122A and 122B in the present embodiment as well as in the second embodiment. In the present embodiment, the unit insertion tube 78 extends from the inside of the motor casing 121 to the inside of the holding casing 77. Inside the holding casing 77, the proximal end of the unit channel tube 75 is connected to the unit insertion tube 78. As in the second embodiment, the driving source unit 81 is provided inside the motor casing 121.

In the driving source unit 81, a bevel, wheel 150 is attached to the motor shaft 108A of the motor 82 which is the driving source. The bevel wheel 150 includes a wheel 151 attached to the motor shaft 108A, and a wheel 152 which meshes with the wheel 151. When the motor 82 is driven, the wheel 151 rotates around the motor axis M together with the motor shaft 108A. The wheel 152 rotates around a rotation axis (transmission rotation axis) R4 perpendicular to the motor axis M in response to the rotation of the wheel 151.

As shown in FIG. 19 to FIG. 21, a shaft member 153 is attached to the motor casing 121. The wheel 152 of the bevel wheel 150 is fixed to the shaft member 153 which serves as the driving source side actuation portion. Therefore, in response to the rotation of the wheel 151, the shaft member 153 rotates around the rotation axis (transmission rotation axis) R4 together with the wheel 152. The shaft member 153 extends from the inside of the motor casing 121 to the outside of the motor casing 121. The shaft member 153 includes an engagement head 155 located outside the motor casing 121. The section of the engagement head 155 perpendicular to the rotation axis R4 is substantially octagonal.

When the motor 82 which is the driving source is driven, the generated rotation driving force is transmitted to the shaft member 153 which serves as the driving source side actuation portion by the bevel wheel 150. That is, the bevel wheel 150 serves as the driving source side transmission portion configured to transmit the rotation driving force to the shaft member 153 which serves as the driving source side actuation portion from the motor 82. When the rotation driving force is transmitted, the shaft member 153 is actuated, and rotates around the rotation axis (transmission rotation axis) R4. That is, the shaft member 153 is the driving source side rotation portion which is actuated to rotate around the rotation axis (transmission rotation axis) R4.

FIG. 22 is a diagram showing the configuration of the driving force transmitting unit (attachment unit) 85. As shown in FIG. 22, the driving force transmitting unit 85 includes the drive shaft 86, the intermediary member 142, and the rotation gear 95, as in the second embodiment. When the driving force transmitting unit 85 is attached to the insertion section 2 and the holding section 3 and connected to the rotary cylindrical body 65 which serves as the actuation unit, the drive shaft 86 which serves as the line portion extends through the unit channel 76. When the driving force transmitting unit 85 is connected to the rotary cylindrical body 65, the channel axis P of the unit channel 76 is coaxial with the driving axis G of the driving force transmitting unit 85.

In the present embodiment, the driving force transmitting unit 85 includes a case member 156. Intermediate gears 157 and 158 are attached to the case member 156. The intermediate gear 158 is in mesh with the intermediate gear 157. The proximal end of the drive shaft 86 is fixed to the intermediate gear 158 inside the case member 156. The intermediate gear 157 is provided with an engagement recess 159 which is engageable with the engagement head 155 of the shaft member 153. When the engagement protrusion 97 of the rotation gear 95 is engaged with the engagement slot 101 of the base member 57 and when the engagement head 155 of the shaft member 153 is engaged with the engagement recess 159 of the intermediate gear 157, the driving force transmitting unit (attachment unit) 85 is attached to the insertion section 2 and the holding section 3.

The intermediate gear 158 is rotatable around the driving axis G of the driving force transmitting unit 85. The intermediate gear 157 is rotatable around a rotation axis R5 parallel to the driving axis G. FIG. 23 is a sectional view taken along the line 23-23 in FIG. 22. As shown in FIG. 23, the section of the engagement recess 159 of the intermediate gear 157 perpendicular to the rotation axis R5 is substantially octagonal. The shape of the engagement recess 159 of the intermediate gear 157 in the section perpendicular to the rotation axis R5 corresponds to the shape of the engagement head 155 of the shaft member 153 in the section perpendicular to the rotation axis R4. Thus, the engagement recess 159 of the intermediate gear 157 is engageable with the engagement head 155 of the shaft member 153. When the driving force transmitting unit 85 is attached to the insertion section 2 and the holding section 3, the rotation axis R5 of the intermediate gear 157 is coaxial with the rotation axis (transmission rotation axis) R4 of the shaft member 153.

As described above, in the present embodiment, the engagement head 155 of the shaft member 153 serves as the driving source side connection portion. The engagement recess 159 of the intermediate gear 157 serves as the attachment side connection portion to be connected to the driving source side connection portion (155) when the driving force transmitting unit 85 is attached to the insertion section 2 and the holding section 3. In the present embodiment, the attachment side connection portion (159) is connected to the driving source side connection portion (155) outside the unit channel 76.

When the engagement head 155 of the shaft member 153 is engaged with the engagement recess 159 of the intermediate gear 157, the rotation driving force can be transmitted to the engagement recess 159 of the driving force transmitting unit 85 from the engagement head 155 of the driving source unit 81. That is, the engagement recess 159 serves as the driving force receiving portion configured to receive the rotation driving force from the driving source unit 81. The engagement recess 159 is provided to the proximal direction side with respect to the drive shaft 86 (line portion). When the driving force transmitting unit 85 is attached to the insertion body assembly 1B, the engagement recess 159 which serves as the driving force receiving portion is located and set at the position to receive the rotation driving force from the driving source unit 81.

When the driving force transmitting unit 85 is attached to the insertion section 2 and the holding section 3, the intermediate gear 157 receives the rotation driving force from the shaft member 153 in response to the rotation of the shaft member 153 which serves as the driving source side actuation portion. As a result, the intermediate gear 157 rotates around the rotation axis (transmission rotation axis) R4 together with the shaft member 153. That is, the intermediate gear 157 is the attachment side actuation portion which receives the rotation driving force from the driving source side actuation portion (153) and is actuated by the actuation of the driving source side actuation portion (153) when the driving force transmitting unit 85 is attached to the insertion section 2 and the holding section 3. The intermediate gear 157 is also an attachment side rotation portion which rotates around the rotation axis (transmission rotation axis) R4 by being actuated when the driving force transmitting unit 85 is attached to the insertion section 2 and the holding section 3. The driving force receiving portion (159) is provided in the attachment side rotation portion (157).

When the intermediate gear 157 rotates around the rotation axis R4 (R5), the intermediate gear 158 rotates around the driving axis G. When the intermediate gear 158 rotates, rotation driving force is transmitted to the drive shaft 86 from the intermediate gear 157. As a result, the drive shaft 86 which serves as the line portion rotates around the driving axis G. That is, the intermediate gear 158 is an attachment side transmission portion which transmits the rotation driving force to the strand portion (86) and rotates the line portion (86) around the driving axis G in response to the actuation of the attachment side rotation portion (157) when the driving force transmitting unit 85 is attached to the insertion section 2 and the holding section 3. When the drive shaft 86 rotates, the rotation gear 95 rotates around the driving axis G, and the rotary cylindrical body 65 and the rotary unit 30 rotate in one of the directions around the longitudinal axis.

Now, the function and advantageous effects of the endoscope device 1 which is the insertion device according to the present embodiment are described. When the endoscope device 1 is used, the driving force transmitting unit 85 is inserted through the unit channel 76, the engagement protrusion 97 of the rotation gear 95 engages with the engagement slot 101 of the base member 57, and the engagement head 155 of the shaft member 153 engages with the engagement recess 159 of the intermediate gear 157. As a result, the driving force transmitting unit (attachment unit) 85 is attached to the insertion section 2 and the holding section 3. When the driving force transmitting unit 85 is attached to the insertion section 2 and the holding section 3, the rotation gear 95 meshes with the inner peripheral gear portion 102 of the rotary cylindrical body 65. The engagement recess (attachment side connection portion) 159 of the intermediate gear 157 is connected to the engagement head (driving source side connection portion) 155 of the shaft member 153.

The insertion section 2 and the rotary unit 30 are then inserted into the lumen. When the insertion section 2 is inserted in the lumen, an electric power is supplied to the motor 82 from the driving control section 13 by a driving operation in the driving operation input section 15, and the motor 82 is driven. As a result, the rotation driving force to rotate the rotary unit 30 relative to the insertion section 2 in one of the directions around the longitudinal axis is generated. When the motor shaft 108A of the motor 82 rotates around the motor axis M, the rotation driving force is transmitted from the motor 82 to the shaft member 153 which serves as the driving source side actuation portion by the bevel wheel 150 which serves as the driving source side transmission portion. As a result, the shaft member 153 is actuated, and the shaft member 153 rotates around the rotation axis (transmission rotation axis) R4.

Here, the engagement recess 159 of the intermediate gear 157 is connected to the engagement head 155 of the shaft member 153, so that when the shaft member 153 is actuated, the engagement recess 159 which serves as the driving force receiving portion of the intermediate gear 157 receives the rotation driving force from the shaft member 153. As a result, the intermediate gear 157 is actuated, and the intermediate gear 157 rotates around the rotation axis R4 (R5). When the intermediate gear 157 rotates, the rotation driving force is transmitted to the drive shaft 86 which serves as the line portion from the intermediate gear 157 by the intermediate gear 158 which serves as the attachment side transmission portion. As result, the drive shaft 86 rotates around the driving axis G (channel axis P), and the rotation gear 95 rotates around the driving axis G. As a result, the rotary cylindrical body 65 and the rotary unit 30 rotate toward one of the directions around the longitudinal axis.

After the use of the endoscope device 1, the motor 82 which is the driving source is cleaned while being attached to the holding section 3, as in the second embodiment. In this instance, the unit channel 76 is cleaned by the endoscope cleaner while the driving force transmitting unit 85 is removed. The driving force transmitting unit 85 is cleaned separately from the insertion section 2, the holding section 3, and the motor 82. Therefore, as described above in the second embodiment, the cleaning performance for the unit channel 76 can be ensured, and the cleaning performance for the driving force transmitting unit 85 having the drive shaft 86 can be ensured.

When the driving force transmitting unit 85 is attached to the insertion section 2 and the holding section 3, the engagement recess (attachment side connection portion) 159 is connected to the engagement head (driving source side connection portion) 155. That is, when the driving force transmitting unit 85 is inserted through the unit channel 76, the rotation driving force generated in the motor 82 can be transmitted to the drive shaft 86 which serves as the line portion. Therefore, even when the motor 82 which is the driving source is provided in the holding section 3, the driving force transmitting unit 85 having the drive shaft 86 can be easily attached to the insertion section 2 and the holding section 3.

The engagement head (driving source side connection portion) 155 of the shaft member 153 is connected to the engagement recess (attachment side connection portion) 159 of the intermediate gear 157 outside the unit channel 76. That is, in contrast with the second embodiment, the engagement head (driving source side connection portion) 155 of the shaft member 153 and the engagement recess (attachment side connection portion) 159 of the intermediate gear 157 are not provided inside the unit channel 76. Thus, the configuration of the unit channel 76 can be simpler, and the cleaning performance for the unit channel 76 can be improved.

Modification of Third Embodiment

Figure 24:
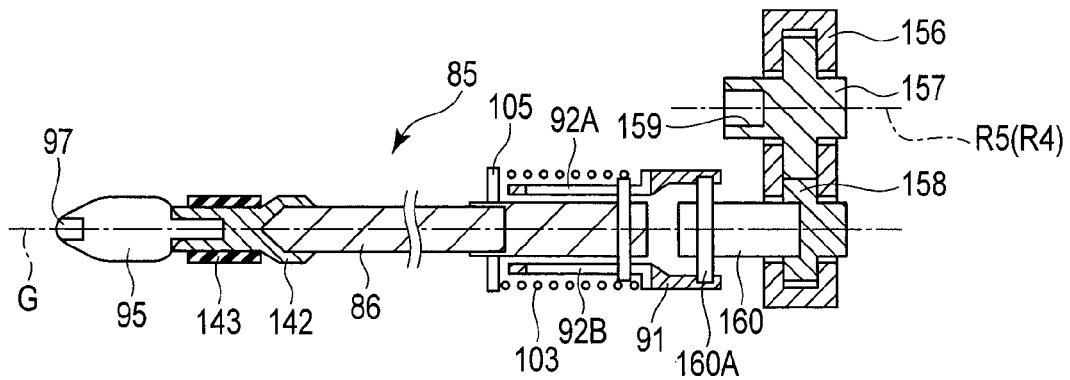
FIG. 24 is a sectional view schematically showing the configuration of the driving force transmitting unit according to a third modification.

As shown in FIG. 24 as a third modification which is a modification of the third embodiment, the intermediary member 87, the slider portion 91, and the elastic member 103 described above in the first embodiment may be provided in the driving force transmitting unit 85 including the case member 156. In the present modification, the drive shaft 86 and the intermediary member 87 serve as the wire portion. The slider portion 91 is attached to the intermediary member 87 movably relative to the strand portion along the driving axis G. The elastic member 103 has its proximal end connected to the slider portion 91 and its distal end connected to the intermediary member 87.

A shaft member 160 is fixed to the intermediate gear 158. The shaft member 160 is fixed to the slider portion 91 via a connection member 160A. As a result, the case member 156, the intermediate gears 157 and 158, and the shaft member 160 are movable relative to the line portion (the drive shaft 86 and the intermediary member 87) along the driving axis G together with the slider portion 91.

In the present modification as well as in the third embodiment, when the engagement recess 159 of the intermediate gear 157 is engaged with the engagement head 155 of the shaft member 153, the driving force transmitting unit 85 is attached to the insertion body assembly 1B.

When the driving force transmitting unit 85 is attached to the insertion body assembly 1B, the slider portion 91 is pressed from the intermediate gear 158 and the shaft member 160 toward the distal direction. When the slider portion 91 is pressed, the slider portion 91 moves toward the distal direction from the state in which the driving force transmitting unit 85 is not attached to the insertion body assembly 1B. In response to the movement of the slider portion 91 in the distal direction, the elastic member 103 contracts from the reference state. As a result, the urging force toward the distal direction is applied to the drive shaft 86, the intermediary member 87 (line portion), and the rotation gear 95 from the elastic member 103 which serves as the urging portion, as in the first embodiment.

Fourth Embodiment

Now, a fourth embodiment of the present invention is described with reference to FIG. 25 to FIG. 29. In the fourth embodiment, the configuration according to the second embodiment is modified as below. The same parts as those in the second embodiment are provided with the same reference numerals, and are not described.

Figure 25:
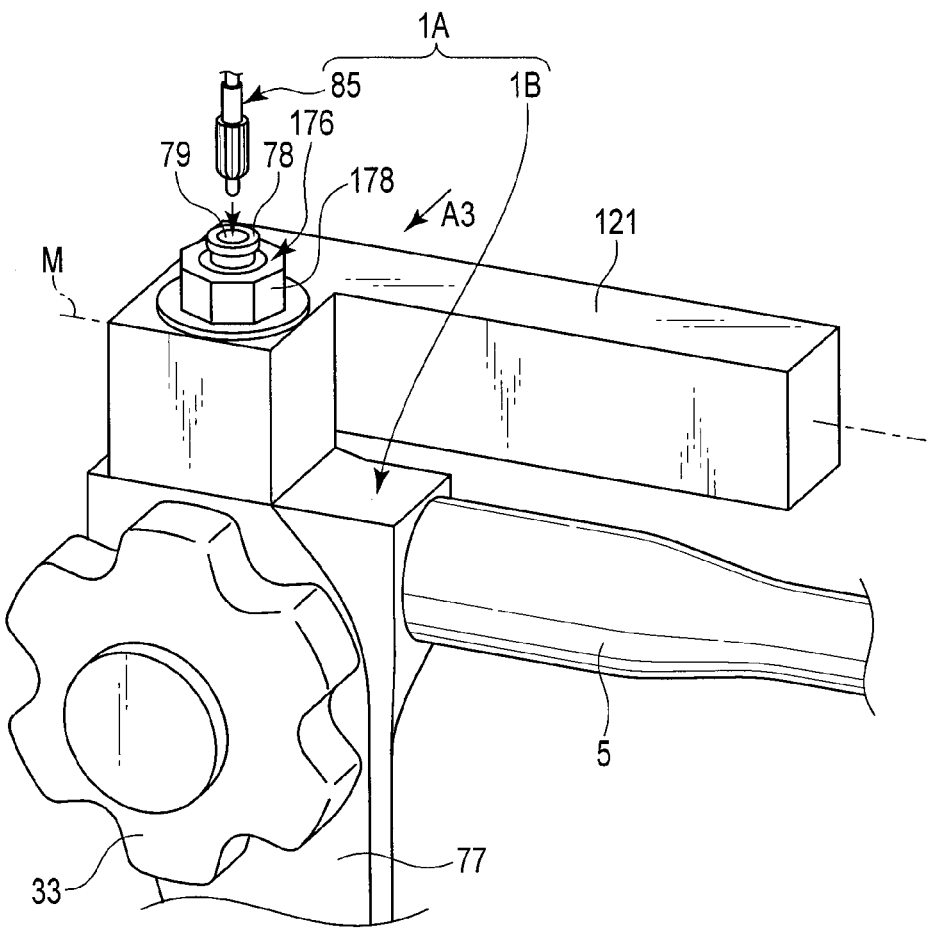
FIG. 25 is a perspective view schematically showing the configuration of the holding section according to a fourth embodiment.
Figure 26:
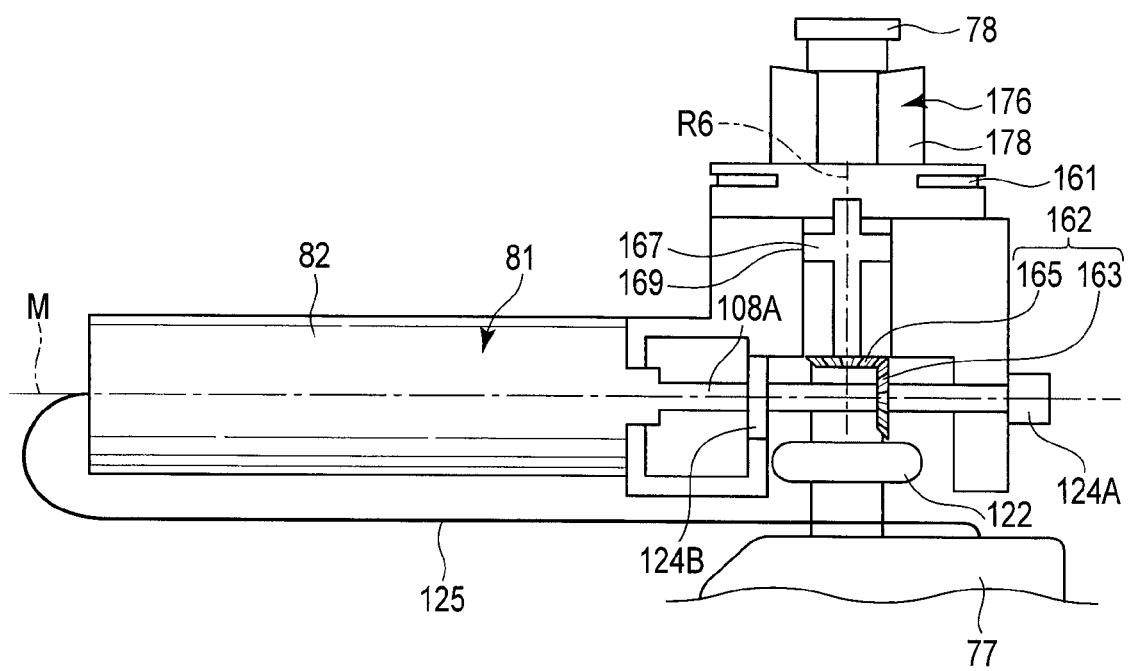
FIG. 26 is a schematic diagram showing the internal configuration of the motor casing of the holding section when seen from an arrow A3 direction in FIG. 25 according to the fourth embodiment.

FIG. 25 is a diagram showing the configuration of the holding section 3 according to the present embodiment. FIG. 26 and FIG. 27 are diagrams showing the internal configuration of the motor casing 121 of the holding section 3. Here, FIG. 26 is a diagram showing the inside of the motor casing 121 when seen from the direction of an arrow A3 in FIG. 25, and FIG. 27 is a diagram showing a section through the unit channel 76. As shown in FIG. 26 and FIG. 27, the unit insertion tube 78 is fixed to the motor casing 121 via a seal ring 122 in the present embodiment as well as in the second embodiment. In the present embodiment, the unit insertion tube 78 extends from the inside of the motor casing 121 to the inside of the holding casing 77. Inside the holding casing 77, the proximal end of the unit channel tube 75 is connected to the unit insertion tube 78. Engagement slots 161 are provided on the outer surface of the unit insertion tube 78. As in the second embodiment, the driving source unit 81 is provided inside the motor casing 121.

The driving source unit 81 includes the motor 82 which is the driving source. A bevel wheel 162 is attached to the motor shaft 108A of the motor 82. The bevel wheel 162 includes a wheel 163 attached to the motor shaft 108A, and a wheel 165 which meshes with the wheel 163. When the motor 82 is driven, the wheel 163 rotates around the motor axis M together with the motor shaft 108A. The wheel 165 rotates around a rotation axis R6 perpendicular to the motor axis M in response to the rotation of the wheel 163.

A shaft member 167 is attached to the unit insertion tube 78 and the motor casing 121. The wheel 165 of the bevel wheel 162 is fixed to the shaft member 167. Therefore, in response to the rotation of the wheel 163, the shaft member 167 rotates around the rotation axis R6 together with the wheel 165. An outer peripheral gear portion 169 is provided on the outer peripheral portion of the shaft member 167.

Intermediate gears 172 and 173 are attached to the unit insertion tube 78 via a coupling pin 171. The intermediate gear 172 meshes with the outer peripheral gear portion 169 of the shaft member 167. Thus, when the shaft member 167 rotates, the intermediate gear 172 rotates around a rotation axis R7. When the intermediate gear 172 rotates, the coupling pin 171 and the intermediate gear 173 rotate around the rotation axis R7 together with the intermediate gear 172.

A cylindrical member 176 which serves as the driving source side actuation portion is attached to the unit insertion tube 78 via seal rings 175A and 175B. The unit insertion tube 78 is inserted through the cylindrical member 176. An inner peripheral gear portion 177 which meshes with the intermediate gear 173 is provided on the inner peripheral portion of the cylindrical member 176. Thus, in response to the rotation of the intermediate gear 173, the cylindrical member 176 rotates around a rotation axis (transmission rotation axis) R8. Here, the rotation axis (transmission rotation axis) R8 of the cylindrical member 176 is coaxial with the channel axis P of the unit channel 76. A driving source side engagement surface (driving source side connection portion) 178 is provided on the outer peripheral portion of the cylindrical member 176. The section of the driving source side engagement surface 178 perpendicular to the rotation axis (transmission rotation axis) R8 is substantially octagonal.

When the motor 82 which is the driving source is driven, the generated rotation driving force is transmitted to the cylindrical member 176 which serves as the driving source side actuation portion by the bevel wheel 162, the coupling pin 171, and the intermediate gears 172 and 173. That is, the bevel wheel 162, the coupling pin 171, and the intermediate gears 172 and 173 serve as the driving source side transmission portion configured to transmit the rotation driving force to the cylindrical member 176 which serves as the driving source side actuation portion from the motor 82. When the rotation driving force is transmitted, the cylindrical member 176 is actuated, and rotates around the rotation axis (transmission rotation axis) R8. That is, the cylindrical member 176 is the driving source side rotation portion which is actuated to rotate around the rotation axis (transmission rotation axis) R8.

FIG. 28 is a diagram showing the configuration of the driving force transmitting unit (attachment unit) 85. As shown in FIG. 28, the driving force transmitting unit 85 includes the drive shaft 86, the intermediary member 142, and the rotation gear 95, as in the second embodiment. When the driving force transmitting unit 85 is attached to the insertion section 2 and the holding section 3, the drive shaft 86 which serves as the line portion extends through the unit channel 76. When the driving force transmitting unit 85 is connected to the rotary cylindrical body 65 which serves as the actuation unit, the channel axis P of the unit channel 76 is coaxial with the driving axis G of the driving force transmitting unit 85. Therefore, when the driving force transmitting unit 85 is attached to the insertion section 2 and the holding section 3, the rotation axis (transmission rotation axis) R8 of the cylindrical member 176 is coaxial with the driving axis G of the driving force transmitting unit 85.

Figure 29:
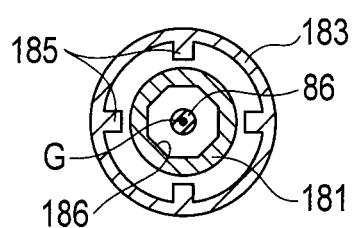
FIG. 29 is a sectional view taken along the line 29-29 in FIG. 28.

FIG. 29 is a sectional view taken along the line 29-29 in FIG. 28. As shown in FIG. 28 and FIG. 29, the proximal end of the drive shaft 86 is fixed to an intermediary member 181. A cylindrical coupling member 183 is attached to the intermediary member 181 via a C-shaped ring 182. The drive shaft 86 and the intermediary member 181 are rotatable relative to the coupling member 183 around the driving axis G.

Engagement claws 185 are provided in the coupling member 183. Each of the engagement claws 185 is engageable with a corresponding engagement slot 161 of the unit insertion tube 78. The engagement protrusion 97 of the rotation gear 95 engages with the engagement slot 101 of the base member 57, and each of the engagement claws 185 engages with the corresponding engagement slot 161, so that the driving force transmitting unit 85 is attached to the insertion section 2 and the holding section 3. When the driving force transmitting unit 85 is attached to the insertion section 2 and the holding section 3, the coupling member 183 is fixed to the unit insertion tube 78.

An attachment side engagement surface (attachment side connection portion) 186 is provided on the intermediary member 181. The section of the attachment side engagement surface 186 perpendicular to the driving axis G (rotation axis R8) is substantially octagonal. The shape of the attachment side engagement surface 186 of the intermediary member 181 in the section perpendicular to the driving axis G corresponds to the shape of the driving source side engagement surface 178 of the cylindrical member 176 in the section perpendicular to the rotation axis R8. Thus, the attachment side engagement surface 186 of the intermediary member 181 is engageable with the driving source side engagement surface 178 of the cylindrical member 176.

As described above, the driving source side engagement surface 178 of the cylindrical member 176 serves as the driving source side connection portion. The attachment side engagement surface 186 of the intermediary member 181 serves as the attachment side connection portion to be connected to the driving source side connection portion (178) when the driving force transmitting unit 85 is attached to the insertion section 2 and the holding section 3. In the present embodiment, the attachment side connection portion (186) is connected to the driving source side connection portion (178) outside the unit channel 76.

When the driving source side engagement surface 178 of the cylindrical member 176 is engaged with the attachment side engagement surface 186 of the intermediary member 181, the rotation driving force can be transmitted to the attachment side engagement surface 186 of the driving force transmitting unit 85 from the driving source side engagement surface 178 of the driving source unit 81. That is, the attachment side engagement surface 186 serves as the driving force receiving portion configured to receive the rotation driving force from the driving source unit 81. The attachment side engagement surface 186 is provided to the proximal direction side with respect to the drive shaft 86 (strand portion). When the driving force transmitting unit 85 is attached to the insertion body assembly 1B, the attachment side engagement surface 186 which serves as the driving force receiving portion is located and set at the position to receive the rotation driving force from the driving source unit 81.

When the driving force transmitting unit 85 is attached to the insertion section 2 and the holding section 3, the intermediary member 181 receives the rotation driving force from the cylindrical member 176 in response to the rotation of the cylindrical member 176 which serves as the driving source side actuation portion. As a result, the intermediary member 181 rotates around the driving axis G (rotation axis R8) together with the cylindrical member 176. That is, the intermediary member 181 is the attachment side actuation portion which receives the rotation driving force from the driving source side actuation portion (176) and is actuated by the actuation of the driving source side actuation portion (176) when the driving force transmitting unit 85 is attached to the insertion section 2 and the holding section 3. The intermediary member 181 is also an attachment side rotation portion which rotates around the rotation axis (transmission rotation axis) R8 by being actuated when the driving force transmitting unit 85 is attached to the insertion section 2 and the holding section 3. The driving force receiving portion (186) is provided in the attachment side rotation portion (181).

When the intermediary member 181 rotates around the rotation axis R8 (driving axis G), the rotation driving force is transmitted to the drive shaft 86 from the intermediary member 181. As a result, the drive shaft 86 which serves as the wire portion rotates around the driving axis G. That is, the intermediary member 181 is an attachment side transmission portion which is configured to transmit the rotation driving force to the strand portion (86) and rotates the line portion (86) around the driving axis G in response to the actuation of the attachment side rotation portion (181) when the driving force transmitting unit 85 is attached to the insertion body assembly 1B. When the drive shaft 86 rotates, the rotation gear 95 rotates around the driving axis G, and the rotary cylindrical body 65 and the rotary unit 30 rotate toward one of the directions around the longitudinal axis.

Now, the function and advantageous effects of the endoscope device 1 which is the insertion device according to the present embodiment are described. When the endoscope device 1 is used, the driving force transmitting unit (attachment unit) 85 is inserted into the unit channel 76, so that the engagement protrusion 97 of the rotation gear 95 engages with the engagement slot 101 of the base member 57, and each of the engagement claws 185 of the coupling member 183 engages with the corresponding engagement slot 161 of the unit insertion tube 78. As a result, the driving force transmitting unit 85 is attached to the insertion section 2 and the holding section 3. When the driving force transmitting unit 85 is attached to the insertion section 2 and the holding section 3, the rotation gear 95 meshes with the inner peripheral gear portion 102 of the rotary cylindrical body 65. The attachment side engagement surface (attachment side connection portion) 186 of the intermediary member 181 is connected to the driving source side engagement surface (driving source side connection portion) 178 of the cylindrical member 176.

The insertion section 2 and the rotary unit 30 are then inserted into the lumen. When the insertion section 2 is inserted in the lumen, an electric power is supplied to the motor 82 from the driving control section 13 by a driving operation in the driving operation input section 15, and the motor 82 is driven. As a result, the rotation driving force to rotate the rotary unit 30 relative to the insertion section 2 toward one of the directions around the longitudinal axis is generated. When the motor shaft 108A of the motor 82 rotates around the motor axis M, the rotation driving force is transmitted to the cylindrical member 176 which serves as the driving source side actuation portion by the bevel wheel 162, the coupling pin 171, and the intermediate gears 172 and 173 which serve as the driving source side transmission portion. As a result, the cylindrical member 176 is actuated, and the cylindrical member 176 rotates around the rotation axis (transmission rotation axis) R8.

Here, the attachment side engagement surface 186 of the intermediary member 181 is connected to the driving source side engagement surface 178 of the cylindrical member 176, so that when the cylindrical member 176 is actuated, the attachment side engagement surface 186 which serves as the driving force receiving portion of the intermediary member 181 receives the rotation driving force from the cylindrical member 176. As a result, the intermediary member 181 is actuated, and the intermediary member 181 rotates around the rotation axis R8 (driving axis G). When the intermediary member 181 rotates, the rotation driving force is transmitted to the drive shaft 86 which serves as the wire portion from the intermediary member 181. As a result, the drive shaft 86 rotates around the driving axis G (channel axis P), and the rotation gear 95 rotates around the driving axis G. As a result, the rotary cylindrical body 65 and the rotary unit 30 rotate toward one of the directions around the longitudinal axis.

After the use of the endoscope device 1, the motor 82 which is the driving source is cleaned while being attached to the holding section 3, as in the second embodiment. In this instance, the unit channel 76 is cleaned by the endoscope cleaner while the driving force transmitting unit 85 is removed. The driving force transmitting unit 85 is cleaned separately from the insertion section 2, the holding section 3, and the motor 82. Therefore, as described above in the second embodiment, the cleaning performance for the unit channel 76 can be ensured, and the cleaning performance for the driving force transmitting unit 85 having the drive shaft 86 can be ensured.

When the driving force transmitting unit 85 is attached to the insertion section 2 and the holding section 3, the attachment side engagement surface (attachment side connection portion) 186 is connected to the driving source side engagement surface (driving source side connection portion) 178. That is, when the driving force transmitting unit 85 is inserted through the unit channel 76, the rotation driving force generated in the motor 82 can be transmitted to the drive shaft 86 which serves as the line portion. Therefore, even when the motor 82 which is the driving source is provided in the holding section 3, the driving force transmitting unit 85 having the drive shaft 86 can be easily attached to the insertion section 2 and the holding section 3.

The rotation axis R8 of the cylindrical member 176 provided with the driving source side engagement surface (driving source side connection portion) 178 and the intermediary member 181 provided with the attachment side engagement surface (attachment side connection portion) 186 is coaxial with the driving axis G of the driving force transmitting unit 85 when the driving force transmitting unit 85 is attached to the insertion section 2 and the holding section 3. The rotation axis (transmission rotation axis) R8 is coaxial with the driving axis G (channel axis P) of the driving force transmitting unit 85 when the driving force transmitting unit 85 is attached to the insertion section 2 and the holding section 3, so that the configuration of the driving force transmitting unit 85 can be simpler.

The driving source side engagement surface (driving source side connection portion) 178 of the cylindrical member 176 is connected to the attachment side engagement surface (attachment side connection portion) 186 of the intermediary member 181 outside the unit channel 76. That is, in contrast with the second embodiment, the driving source side engagement surface (driving source side connection portion) 178 of the cylindrical member 176 and the attachment side engagement surface (attachment side connection portion) 186 of the intermediary member 181 are not provided inside the unit channel 76. Thus, the configuration of the unit channel 76 can be simpler, and the cleaning performance for the unit channel 76 can be improved.

Modification of Fourth Embodiment

Figure 30:
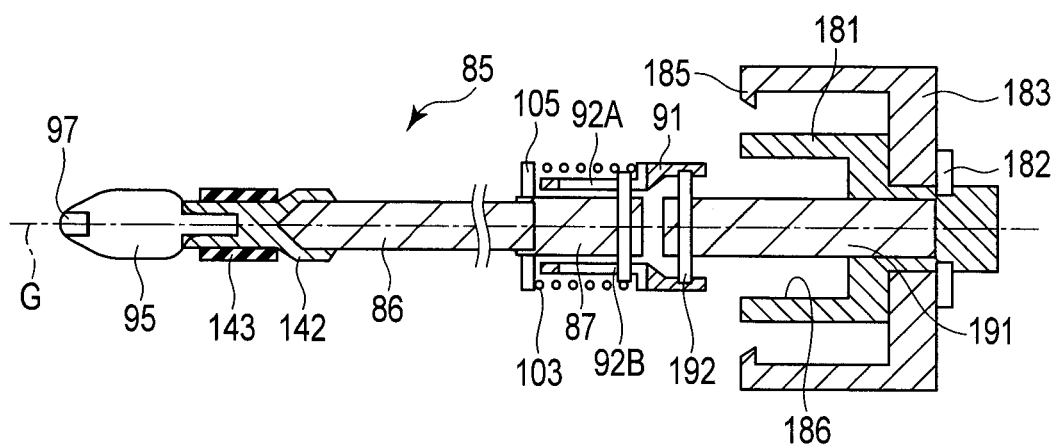
FIG. 30 is a sectional view schematically showing the configuration of the driving force transmitting unit according to a fourth modification.

As shown in FIG. 30 as a fourth modification which is a modification of the fourth embodiment, the intermediary member 87, the slider portion 91, and the elastic member 103 described above in the first embodiment may be provided in the driving force transmitting unit 85 including the intermediary member 181. In the present modification, the drive shaft 86 and the intermediary member 87 serve as the line portion. The slider portion 91 is attached to the intermediary member 87 movably relative to the line portion along the driving axis G. The elastic member 103 has its proximal end connected to the slider portion 91 and its distal end connected to the intermediary member 87.

A shaft member 191 is fixed to the intermediary member 181. The shaft member 191 is fixed to the slider portion 91 via a connection member 92. As a result, the intermediary member 181, the ring 182, and the coupling member 183 are movable relative to the strand portion (the drive shaft 86 and the intermediary member 87) along the driving axis G together with the slider portion 91.

In the present modification as well as in the fourth embodiment, when each of the engagement claws 185 is engaged with a corresponding engagement slot 161 of the unit insertion tube 78, the driving force transmitting unit 85 is attached to the insertion body assembly 1B.

When the driving force transmitting unit 85 is attached to the insertion body assembly 1B, the slider portion 91 is pressed from the intermediary member 181 and the shaft member 191 toward the distal direction. When the slider portion 91 is pressed, the slider portion 91 moves toward the distal direction from the state in which the driving force transmitting unit 85 is not attached to the insertion body assembly 1B. In response to the movement of the slider portion 91 in the distal direction, the elastic member 103 contracts from the reference state. As a result, the urging force toward the distal direction is applied to the drive shaft 86, the intermediary member 87 (line portion), and the rotation gear 95 from the elastic member 103 which serves as the urging portion, as in the first embodiment.

Fifth Embodiment

Now, a fifth embodiment of the present invention is described with reference to FIG. 31 and FIG. 32. In the fifth embodiment, the configuration according to the second embodiment is modified as below. The same parts as those in the second embodiment are provided with the same reference numerals, and are not described.

FIG. 31 is a diagram showing the configuration of the holding section 3 and the driving force transmitting unit (attachment unit) 85. Here, FIG. 31 is a diagram showing a section through the unit channel 76. As shown in FIG. 31, the unit insertion tube 78 is fixed to the motor casing 121 via the seal ring 122 in the present embodiment as well as in the second embodiment. In the present embodiment, the unit insertion tube 78 extends from the inside of the motor casing 121 to the inside of the holding casing 77. Inside the holding casing 77, the proximal end of the unit channel tube 75 is connected to the unit insertion tube 78.

As in the second embodiment, the driving source unit 81 is provided inside the motor casing 121. An intermediate gear 195 is attached to the motor shaft 108A of the motor 82 which is the driving source of the driving source unit 81. When the motor 82 is driven, the intermediate gear 195 rotates around the motor axis M together with the motor shaft 108A of the motor 82.

A cylindrical member 197 which serves as the driving source side actuation portion is attached to the unit insertion tube 78 via a bearing 196. The unit insertion tube 78 is inserted through the cylindrical member 197. An outer peripheral gear portion 198 which meshes with the intermediate gear 195 is provided on the outer peripheral portion of the cylindrical member 197. Thus, in response to the rotation of the intermediate gear 195, the cylindrical member 197 rotates around a rotation axis (transmission rotation axis) R9. Here, the rotation axis (transmission rotation axis) R9 of the cylindrical member 197 is coaxial with the channel axis P of the unit channel 76.

A driving source side magnet 201 is provided in the cylindrical member 197. FIG. 32 is a diagram showing the configurations of the driving source side magnet 201 and a later-described attachment side magnet 211. As shown in FIG. 31 and FIG. 32, the driving source side magnet 201 is ring-shaped, and the unit insertion tube 78 is inserted through the driving source side magnet 201. The driving source side magnet 201 is located inside the motor casing 121 (inside the holding section 3). The driving source side magnet 201 includes two driving source side positive poles 202A and 202B, and two driving source side negative poles 203A and 203B. The driving source side N poles 202A and 202B are located at angular positions about 180 degrees apart from each other in directions around the channel axis. Each of the driving source side S poles 203A and 203B is located between the driving source side positive pole 202A and the driving source side positive pole 202B. The driving source side negative poles 203A and 203B are located at angular positions about 180 degrees apart from each other in the directions around the channel axis.

As described above, when the motor 82 which is the driving source is driven, the generated rotation driving force is transmitted to the cylindrical member 197 which serves as a driving source side actuation portion by the intermediate gear 195. That is, the intermediate gear 195 serves as the driving source side transmission portion configured to transmit the rotation driving force to the cylindrical member 197 which serves as the driving source side actuation portion from the motor 82. When the rotation driving force is transmitted, the cylindrical member 197 is actuated, and rotates around the rotation axis (transmission rotation axis) R9. That is, the cylindrical member 197 is the driving source side rotation portion which is actuated to rotate around the rotation axis (transmission rotation axis) R9.

The driving force transmitting unit 85 includes the drive shaft 86, the intermediary member 142, and the rotation gear 95, as in the second embodiment. When the driving force transmitting unit 85 is attached to the insertion section 2 and the holding section 3, the drive shaft 86 which serves as the wire portion extends through the unit channel 76. When the driving force transmitting unit 85 is connected to the rotary cylindrical body 65 which serves as the actuation unit, the channel axis P of the unit channel 76 is coaxial with the driving axis G of the driving force transmitting unit 85. Therefore, when the driving force transmitting unit 85 is attached to the insertion section 2 and the holding section 3, the rotation axis (transmission rotation axis) R9 of the cylindrical member 197 is coaxial with the driving axis G of the driving force transmitting unit 85.

In the present embodiment, the proximal end of the drive shaft 86 is fixed to a coupling member 205. An engagement slot 206 is provided in the coupling member 205. When the engagement protrusion 97 of the rotation gear 95 is engaged with the engagement slot 101 of the base member 57 and when the unit insertion tube 78 is engaged with the engagement slot 206, the driving force transmitting unit 85 is attached to the insertion section 2 and the holding section 3. When the driving force transmitting unit 85 is attached to the insertion section 2 and the holding section 3, the coupling member 205 is rotatable relative to the unit insertion tube 78 around the driving axis G.

The attachment side magnet 211 is provided in the coupling member 205. The attachment side magnet 211 is ring-shaped, and is located to face the driving source side magnet 201. The driving source side magnet 201 is isolated from the attachment side magnet 211 by the motor casing 121. Therefore, the attachment side magnet 211 is located outside the holding section 3 (outside the motor casing 78). The attachment side magnet 211 includes two attachment side positive poles 212A and 212B, and two attachment side negative poles 213A and 213B. The attachment side N poles 212A and 212B are located at angular positions about 180 degrees apart from each other in directions around the driving axis. Each of the attachment side S poles 213A and 213B is located between the attachment side positive pole 212A and the attachment side positive pole 212B. The attachment side negative poles 213A and 213B are located at angular positions about 180 degrees apart from each other in the directions around the driving axis.

When the driving force transmitting unit 85 is attached to the insertion section 2 and the holding section 3, the attachment side negative pole 213A faces the driving source side positive pole 202A, and the attachment side negative pole 213B faces the driving source side positive pole 202B. The attachment side positive pole 212A faces the driving source side negative pole 203A, and the attachment side positive pole 212B faces the driving source side negative pole 203B.

In response to the rotation of the cylindrical member 197 when the driving force transmitting unit 85 is attached to the insertion section 2 and the holding section 3, the coupling member 205 rotates around the driving axis G (rotation axis R9) by the magnetic force between the driving source side magnet 201 and the attachment side magnet 211. As a result, the coupling member 205 receives the rotation driving force from the cylindrical member 197 by the magnetic force between the driving source side magnet 201 and the attachment side magnet 211 without connection between the cylindrical member (driving source side actuation portion) 197 and the coupling member (attachment side actuation portion) 205. Here, the coupling member 205 is an attachment side actuation portion which receives the rotation driving force from the driving source side actuation portion (197) and is actuated by the actuation of the driving source side actuation portion (197) when the driving force transmitting unit 85 is attached to the insertion section 2 and the holding section 3. The coupling member 205 is also an attachment side rotation portion which rotates around the rotation axis (transmission rotation axis) R9 by being actuated when the driving force transmitting unit 85 is attached to the insertion section 2 and the holding section 3.

When the unit insertion tube 78 is engaged with the engagement slot 206 of the coupling member 205, the rotation driving force can be transmitted to the attachment side magnet 211 of the coupling member 205 from the driving source side magnet 201 of the cylindrical member 197. That is, the attachment side magnet 211 serves as the driving force receiving portion configured to receive the rotation driving force from the driving source unit 81. The attachment side magnet 211 is provided to the proximal direction side with respect to the drive shaft 86 (line portion). When the driving force transmitting unit 85 is attached to the insertion body assembly 1B, the attachment side magnet 211 which serves as the driving force receiving portion is located and set at the position to receive the rotation driving force from the driving source unit 81. The driving force receiving portion (211) is provided in the attachment side rotation portion (205).

When the coupling member 205 rotates around the rotation axis R9 (driving axis G), the rotation driving force is transmitted to the drive shaft 86 from the coupling member 205. As a result, the drive shaft 86 which serves as the strand portion rotates around the driving axis G. That is, the coupling member 205 is an attachment side transmission portion which is configured to transmit the rotation driving force to the line portion (86) and rotates the line portion (86) around the driving axis G in response to the actuation of the attachment side rotation portion (205) when the driving force transmitting unit 85 is attached to the insertion section 2 and the holding section 3. When the drive shaft 86 rotates, the rotation gear 95 rotates around the driving axis G, and the rotary cylindrical body 65 and the rotary unit 30 rotate toward one of the directions around the longitudinal axis.

Now, the function and advantageous effects of the endoscope device 1 which is the insertion device according to the present embodiment are described. When the endoscope device 1 is used, the driving force transmitting unit (attachment unit) 85 is inserted through the unit channel 76, so that the engagement protrusion 97 of the rotation gear 95 engages with the engagement slot 101 of the base member 57, and the engagement slot 206 of the coupling member 205 engages with the unit insertion tube 78. As a result, the driving force transmitting unit 85 is attached to the insertion section 2 and the holding section 3. When the driving force transmitting unit 85 is attached to the insertion section 2 and the holding section 3, the rotation gear 95 meshes with the inner peripheral gear portion 102 of the rotary cylindrical body 65. The attachment side negative pole 213A faces the driving source side positive pole 202A, and the attachment side negative pole 213B faces the driving source side positive pole 202B. The attachment side positive pole 212A faces the driving source side negative pole 203A, and the attachment side positive pole 212B faces the driving source side negative pole 203B.

The insertion section 2 and the rotary unit 30 are then inserted into the lumen. When the insertion section 2 is inserted in the lumen, the electric power is supplied to the motor 82 from the driving control section 13 by a driving operation in the driving operation input section 15, and the motor 82 is driven. As a result, the rotation driving force to rotate the rotary unit 30 relative to the insertion section 2 toward one of the directions around the longitudinal axis is generated. When the motor shaft 108A of the motor 82 rotates around the motor axis M, the rotation driving force is transmitted from the motor 82 to the cylindrical member 197 which serves as the driving source side actuation portion by the intermediate gear 195 which serves as the driving source side transmission portion. As a result, the cylindrical member 197 is actuated, and the cylindrical member 197 rotates around the rotation axis (transmission rotation axis) R9.

When the cylindrical member 197 is actuated, the attachment side magnet 211 of the coupling member 205 receives the rotation driving force from the cylindrical member 197 by the magnetic force between the driving source side magnet 201 and the attachment side magnet 211. As a result, without connection between the cylindrical member (driving source side actuation portion) 197 and the coupling member (attachment side actuation portion) 205, the coupling member 205 is actuated, and the coupling member 205 rotates around the rotation axis R9 (driving axis G). When the coupling member 205 rotates, the rotation driving force is transmitted to the drive shaft 86 which serves as the wire portion from the coupling member 205. As a result, the drive shaft 86 rotates around the driving axis G (channel axis P), and the rotation gear 95 rotates around the driving axis G. As a result, the rotary cylindrical body 65 and the rotary unit 30 rotate toward one of the directions around the longitudinal axis.

After the use of the endoscope device 1, the motor 82 which is the driving source is cleaned while being attached to the holding section 3, as in the second embodiment. In this instance, the unit channel 76 is cleaned by the endoscope cleaner while the driving force transmitting unit 85 is removed. The driving force transmitting unit 85 is cleaned separately from the insertion section 2, the holding section 3, and the motor 82. Therefore, as described above in the second embodiment, the cleaning performance for the unit channel 76 can be ensured, and the cleaning performance for the driving force transmitting unit 85 having the drive shaft 86 can be ensured.

When the driving force transmitting unit 85 is attached to the insertion section 2 and the holding section 3, the attachment side negative pole 213A faces the driving source side positive pole 202A, and the attachment side negative pole 213B faces the driving source side positive pole 202B. The attachment side positive pole 212A faces the driving source side negative pole 203A, and the attachment side positive pole 212B faces the driving source side negative pole 203B. That is, when the driving force transmitting unit 85 is inserted through the unit channel 76, the rotation driving force generated in the motor 82 can be transmitted to the drive shaft 86 which serves as the line portion. Therefore, even when the motor 82 which is the driving source is provided in the holding section 3, the driving force transmitting unit 85 including the drive shaft 86 can be easily attached to the insertion section 2 and the holding section 3.

When the press force from the lumen wall toward the inner peripheral direction in the spiral fin portion 31 is great, an anti-rotation force toward a direction opposite to the rotation direction of the rotation driving force generated in the motor 82 is increased in the coupling member (attachment side actuation portion) 205. In the present embodiment, the cylindrical member (driving source side actuation portion) 197 is not connected to the coupling member (attachment side actuation portion) 205. Thus, when the anti-rotation force is increased in the coupling member 205, the coupling member 205 is not rotated by the magnetic force between the driving source side magnet 201 and the attachment side magnet 211 even if the cylindrical member 197 rotates. That is, the coupling member 205 does not receive the rotation driving force from the cylindrical member 197, and does not rotate in response to the cylindrical member 197. Thus, it is possible to effectively prevent the rotation of the drive shaft 86 when the press force from the lumen wall toward the inner peripheral direction in the spiral fin portion 31 is great, and effectively prevent troubles in the driving force transmitting unit 85 and the rotary unit 30.

Modification of Fifth Embodiment

Figure 33:
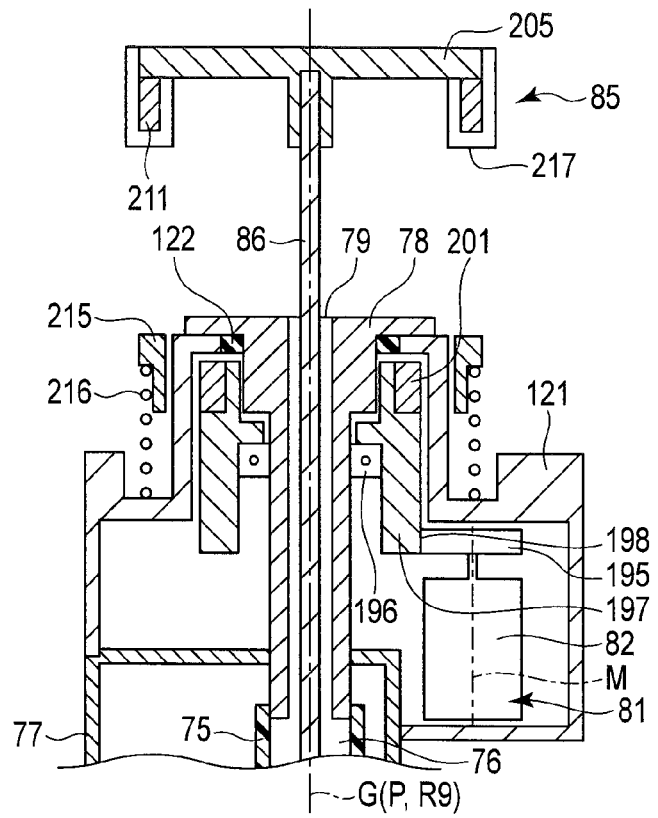
FIG. 33 is a sectional view schematically showing the configurations of the holding section and the driving force transmitting unit when the driving force transmitting unit is not attached to the insertion section and the holding section according to the fifth modification.
Figure 34:
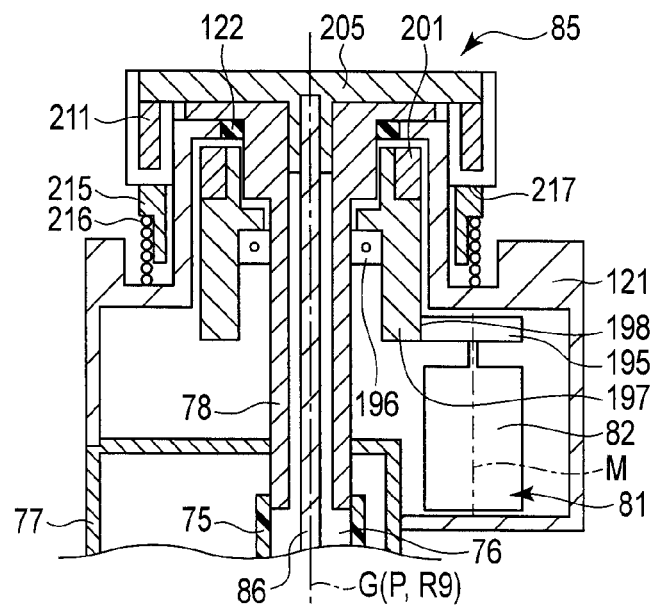
FIG. 34 is a sectional view schematically showing the configurations of the holding section and the driving force transmitting unit when the driving force transmitting unit is attached to the insertion section and the holding section according to the fifth modification.

FIG. 33 and FIG. 34 are diagrams showing the configurations of the holding section 3 and the driving force transmitting unit (attachment unit) 85 according to a fifth modification which is a modification of the fifth embodiment. Here, FIG. 33 and FIG. 34 are diagrams showing a section through the unit channel 76. FIG. 33 shows a state in which the driving force transmitting unit 85 is not attached to the insertion section 2 and the holding section 3. FIG. 34 shows a state in which the driving force transmitting unit 85 is attached to the insertion section 2 and the holding section. As shown in FIG. 33 and FIG. 34, the holding section 3 according to the present modification includes a nonmagnetic member 215 and an urging member 216. The nonmagnetic member 215 is attached to the motor casing 121 via the urging member 216. The nonmagnetic member 215 and the urging member 216 are located outside the holding section 3 (outside the motor casing 121).

As shown in FIG. 33, when the driving force transmitting unit 85 is not attached to the insertion section 2 and the holding section 3, the nonmagnetic member 215 is urged by the urging member 21 toward a blocking position at which the nonmagnetic member faces the driving source side magnet 201. When the nonmagnetic member 215 is located at the blocking position, generation of a magnetic field by the driving source side magnet 201 outside the holding section 3 is prevented. As a result, generation of a magnetic field by the driving source side magnet 201 outside the holding section 3 can be effectively prevented in the use of the endoscope device 1 when the driving force transmitting unit 85 is not attached to the insertion section 2 and the holding section 3. Therefore, medical instruments used simultaneously with the endoscope device 1 are not affected by the magnetic field generated by the driving source side magnet 201.

As shown in FIG. 34, the coupling member 205 of the driving force transmitting unit 85 is provided with a press portion 217 which presses the nonmagnetic member 215 against the urging force from the urging member 216 when the driving force transmitting unit 85 is attached to the insertion section 2 and the holding section. When pressed by the press portion 217, the nonmagnetic member 215 moves from the blocking position. When the driving force transmitting unit 85 is attached to the insertion section 2 and the holding section 3, the attachment side magnet 211 is located to face the driving source side magnet 201.

If the motor 82 is driven when the driving force transmitting unit 85 is attached to the insertion section 2 and the holding section, the rotation driving force generated in the motor 82 is transmitted to the cylindrical member 197 which serves as the driving source side actuation portion, as in the fifth embodiment. The coupling member 205 which serves as the attachment side actuation portion then receives the rotation driving force from the cylindrical member 197 by the magnetic force between the driving source side magnet 201 and the attachment side magnet 211. As a result, the coupling member 205 is actuated, and the coupling member 205 rotates around the driving axis G. When the coupling member 205 rotates, the drive shaft 86 rotates around the driving axis G, and the rotary unit 30 rotates toward one of the directions around the longitudinal axis.

Figure 35:
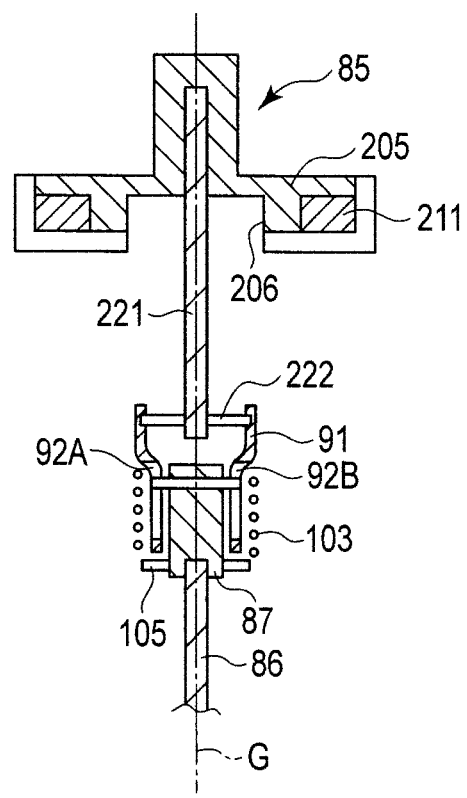
FIG. 35 is a sectional view schematically showing the configuration of the driving force transmitting unit according to a sixth modification.

As shown in FIG. 35 as a sixth modification which is a modification of the fifth embodiment, the intermediary member 87, the slider portion 91, and the elastic member 103 described above in the first embodiment may be provided in the driving force transmitting unit 85 including the attachment side magnet 211. In the present modification, the drive shaft 86 and the intermediary member 87 serve as the strand portion. The slider portion 91 is attached to the intermediary member 87 movably relative to the line portion along the driving axis G. The elastic member 103 has its proximal end connected to the slider portion 91 and its distal end connected to the intermediary member 87.

A shaft member 221 is fixed to the coupling member 205. The shaft member 221 is fixed to the slider portion 91 via a connection member 222. As a result, the coupling member 205 and the attachment side magnet 211 are movable relative to the line portion (the drive shaft 86 and the intermediary member 87) along the driving axis G together with the slider portion 91.

In the present embodiment as well as in the fifth embodiment, when the engagement slot 206 of the coupling member 205 is engaged with the unit insertion tube 78, the driving force transmitting unit 85 is attached to the insertion body assembly 1B.

When the driving force transmitting unit 85 is attached to the insertion body assembly 1B, the slider portion 91 is pressed from the coupling member 205 toward the distal direction. When the slider portion 91 is pressed, the slider portion 91 moves toward the distal direction from the state in which the driving force transmitting unit 85 is not attached to the insertion body assembly 1B. In response to the movement of the slider portion 91 in the distal direction, the elastic member 103 contracts from the reference state. As a result, the urging force toward the distal direction is applied to the drive shaft 86, the intermediary member 87 (strand portion), and the rotation gear 95 from the elastic member 103 which serves as the urging portion, as in the first embodiment.

Other Modifications

In the second to fifth embodiments and their modifications, the holding section 3 includes the driving source (82) which is driven so as to generate the rotation driving force, the driving source side actuation portion (137; 153; 176; 197) which is actuated when the driving source (82) is driven, and the driving source side transmission portion (126, 130, 133; 150; 162, 171, 172, 173; 195) which is configured to transmit the generated rotation driving force to the driving source side actuation portion (137; 153; 176; 197) and to actuate the driving source side actuation portion (137; 153; 176; 197) when the driving source (82) is driven. The driving force transmitting unit (attachment unit) 85 includes the line portion (86; 86, 87) which rotates around the driving axis G and thereby configured to transmit the rotation driving force to rotate the rotary unit 30 to the rotary unit 30. The driving force transmitting unit 85 includes the attachment side actuation portion (145; 157; 181; 205) which is configured to receive the rotation driving force from the driving source side actuation portion (137; 153; 176; 197) and is actuated by the actuation of the driving source side actuation portion (137; 153; 176; 197) when the driving force transmitting unit 85 is attached to the insertion section 2 and the holding section 3, and the attachment side transmission portion (145; 158; 181; 205) which is configured to transmit the rotation driving force to the line portion (86; 86, 87) in response to the actuation of the attachment side transmission portion (145; 157; 181; 205) when the driving force transmitting unit 85 is attached to the insertion section 2 and the holding section 3.

Characteristic technical matters according to the reference examples are additionally set forth below.

Notes (Additional Note 1)

A driving force transmitting unit in an insertion device, the insertion device including an insertion section extending along a longitudinal axis, a rotary unit provided to an outer peripheral side of the insertion section rotatably relative to the insertion section in directions around the longitudinal axis, an actuation unit which is attached to the insertion section and which is configured to be actuated and thereby configured to transmit a rotation driving force to rotate the rotary unit to the rotary unit, and a holding section which is provided to a proximal direction side with respect to the insertion section and in which an insertion hole open to an outside is formed, the driving force transmitting unit being removably attached to the actuation unit when inserted into the holding section and into the insertion section from the insertion hole, the driving force transmitting unit being configured to transmit the rotation driving force to the actuation unit by rotating around a driving axis when the driving force transmitting unit is attached to the actuation unit, the driving force transmitting unit comprising:

a line portion extending through an inside of the insertion section and through an inside of the holding section along the driving axis when the driving force transmitting unit is attached to the actuation unit;

a distal connection portion which is provided in a distal portion of the line portion and which is connected to the actuation unit when the driving force transmitting unit is attached to the actuation unit;

a slider portion which is attached to a proximal portion of the line portion and which is movable relative to the line portion along the driving axis; and an urging portion having a distal end connected to the line portion and a proximal end connected to the slider portion, the urging portion being configured to contract in response to a movement of the slider portion relative to the line portion toward a distal direction and thereby configured to apply an urging force toward the distal direction to the line portion and the distal connection portion.

(Additional Note 2)

The driving force transmitting unit according to Additional note 1, wherein the slider portion includes a driving source connection portion configured to removably connect a driving source, which is driven so as to generate the rotation driving force, to the proximal direction side.

(Additional Note 3)

The driving force transmitting unit according to Additional note 2, wherein in an attached state where a driving force generating unit, which includes the driving source and which is attachable to and detachable from the holding section through the insertion hole, is attached to the holding portion, the slider portion is pressed from the driving force generating unit toward the distal direction and moves toward the distal direction.

(Additional Note 4)

The driving force transmitting unit according to Additional note 3, wherein in an unattached state where the driving force generating unit is not attached to the holding section, the slider portion protrudes to the outside of the holding section from the insertion hole, and in the unattached state, the driving source connection portion is located outside the holding section.

(Additional Note 5)

The driving force transmitting unit according to Additional note 3, wherein in an unattached state where the driving force generating unit is not attached to the holding section, the urging portion is in a reference state, and in the attached state, the urging portion contracts from the reference state.

(Additional Note 6)

The driving force transmitting unit according to Additional note 1, further comprising a driving force generating unit including a driving source which is driven so as to generate the rotation driving force, the driving force generating unit being removably attached to the holding section in the insertion hole, wherein the slider portion includes a driving source connection portion configured to connect the driving source to the proximal direction side.

(Additional Note 7)

The driving force transmitting unit according to Additional note 6, wherein in an attached state where the driving force generating unit is attached to the holding section, the slider portion is pressed from the driving force generating unit toward the distal direction and moves toward the distal direction.

(Additional Note 8)

The driving force transmitting unit according to Additional note 7, wherein in an unattached state where the driving force generating unit is not attached to the holding section, the slider portion protrudes to the outside of the holding section from the insertion hole, and in the unattached state, the driving source connection portion is located outside the holding section.

(Additional Note 9)

The driving force transmitting unit according to Additional note 7, wherein in an unattached state where the driving force generating unit is not attached to the holding section, the urging portion is in a reference state, and in the attached state, the urging portion contracts from the reference state.

(Additional Note 10)

An insertion device comprising:

the driving force transmitting unit according to Additional note 1;

the insertion section;

the rotary unit;

the actuation unit; and the holding section.

(Additional Note 11)

The insertion device according to Additional note 10, further comprising:

a base portion which is provided in the insertion section and to which the rotary unit is attached rotatably in the directions around the longitudinal axis, the base portion defining a cavity in which the distal connection portion is connected to the actuation unit; and a channel defining portion which extends to the cavity from the insertion hole and which defines, inside the insertion section and inside the holding section, a channel through which the driving force transmitting unit is inserted so as to be attached to the actuation unit.

(Additional Note 12)

The insertion device according to Additional note 10, wherein the distal connection portion of the driving force transmitting unit includes a rotation gear rotatable around the driving axis, the actuation unit includes a rotary cylindrical body which is rotatable relative to the insertion section in the directions around the longitudinal axis together with the rotary unit, and the rotary cylindrical body includes an inner peripheral gear portion which is provided over all-round and which meshes with the rotation gear when the driving force transmitting unit is attached to the actuation unit.

(Additional Note 13)

The insertion device according to Additional note 10, wherein the actuation unit includes a rotation gear rotatable around the driving axis, and a rotary cylindrical body which is rotatable relative to the insertion section in the directions around the longitudinal axis together with the rotary unit, the rotary cylindrical body includes an inner peripheral gear portion which is provided over all-round and which meshes with the rotation gear when the driving force transmitting unit is attached, and the distal connection portion is connected to the rotation gear when the driving force transmitting unit is attached to the actuation unit.

(Additional Note 14)

An insertion device comprising:

an insertion section extending along a longitudinal axis from a proximal direction to a distal direction;

a holding section provided to a proximal direction side with respect to the insertion section;

a rotary unit which includes a spiral fin portion spirally extending around the longitudinal axis and which is provided to an outer peripheral side of the insertion section rotatably relative to the insertion section in directions around the longitudinal axis;

a base portion which is provided in the insertion section and to which the rotary unit is attached rotatably relative to the insertion section in the directions around the longitudinal axis;

a channel defining portion which has an insertion hole formed in the holding section and which defines a channel extending to the base portion through an inside of the holding section and through an inside of the insertion section; and an attachment unit which is insertable into the channel from the insertion hole and removable from the channel through the insertion hole and which is attached to the insertion section and the holding section when inserted through the channel, the attachment unit including a line portion which extends through the channel when the attachment unit is attached to the insertion section and the holding section, the line portion being configured to rotate around a driving axis when the attachment unit is attached to the insertion section and the holding section, and thereby configured to transmit a rotation driving force to rotate the rotary unit to the rotary unit, wherein the holding section includes a driving source which is driven so as to generate the rotation driving force, a driving source side actuation portion which is actuated when the driving source is driven, and a driving source side transmission portion which is configured to transmit the generated rotation driving force to the driving source side actuation portion and configured to actuate the driving source side actuation portion when the driving source is driven, and the attachment unit includes an attachment side actuation portion which is configured to receive the rotation driving force from the driving source side actuation portion and configured to be actuated by an actuation of the driving source side actuation portion when the attachment unit is attached to the insertion section and the holding section, and an attachment side transmission portion which is configured to transmit the rotation driving force to the line portion and configured to rotate the line portion around the driving axis in response to an actuation of the attachment side actuation portion when the attachment unit is attached to the insertion section and the holding section.

(Additional Note 15)

The insertion device according to Additional note 14, wherein the driving source side actuation portion includes a driving source side rotation portion which is actuated so as to rotate around a transmission rotation axis, and the attachment side actuation portion includes an attachment side rotation portion which is configured to rotate around the transmission rotation axis by being actuated when the attachment unit is attached to the insertion section and the holding section.

(Additional Note 16)

The insertion device according to Additional note 15, wherein the driving source side rotation portion includes a driving source side connection portion, and the attachment side rotation portion includes an attachment side connection portion which is connected to the driving source side connection portion when the attachment unit is attached to the insertion section and the holding section.

(Additional Note 17)

The insertion device according to Additional note 16, wherein the transmission rotation axis of the driving source side rotation portion and the attachment side rotation portion is coaxial with the driving axis of the line portion when the attachment unit is attached to the insertion section and the holding section, and the attachment side connection portion is connected to the driving source side connection portion inside the channel.

(Additional Note 18)

The insertion device according to Additional note 16, wherein the attachment side connection portion is connected to the driving source side connection portion outside the channel.

(Additional Note 19)

The insertion device according to Additional note 18, wherein the transmission rotation axis of the driving source side rotation portion and the attachment side rotation portion is coaxial with the driving axis of the line portion when the attachment unit is attached to the insertion section and the holding section.

(Additional Note 20)

The insertion device according to Additional note 15, wherein the driving source side rotation portion includes a driving source side magnet, and the attachment side rotation portion includes an attachment side magnet which is configured to rotate the attachment side rotation portion by a magnetic force between the driving source side magnet and the attachment side magnet in response to the rotation of the driving source side rotation portion when the attachment unit is attached to the insertion section and the holding section.

(Additional Note 21)

The insertion device according to Additional note 20, wherein the driving source side magnet is located inside the holding section, and the attachment side magnet is located outside the holding section when the attachment unit is attached to the insertion section and the holding section.

(Additional Note 22)

The insertion device according to Additional note 21, wherein the holding section includes a nonmagnetic member, and an urging member which is configured to urge the nonmagnetic member toward a blocking position in which the nonmagnetic member prevents the generation of a magnetic field by the driving source side magnet outside the holding section, and the attachment unit includes a press portion which presses the nonmagnetic member against an urging from the urging member when the attachment unit is attached to the insertion section and the holding section, and moves the nonmagnetic member from the blocking position.

(Additional Note 23)

The insertion device according to Additional note 14, wherein the attachment unit includes a rotation gear to which a distal end of the line portion is connected, the rotation gear being configured to rotate around the driving axis, and configured to transmit the rotation driving force to the rotary unit from the line portion when the line portion rotates.

(Additional Note 24)

An attachment unit attached town insertion section and a holding section in an insertion device, the insertion device including the insertion section extending along a longitudinal axis from a proximal direction to a distal direction, the holding section provided to a proximal direction side with respect to the insertion section, a rotary unit which includes a spiral fin portion spirally extending around the longitudinal axis and which is provided to an outer peripheral side of the insertion section rotatably relative to the insertion section in directions around the longitudinal axis, a base portion which is provided in the insertion section and to which the rotary unit is attached rotatably relative to the insertion section in the directions around the longitudinal axis, and a channel defining portion which has an insertion hole formed in the holding section and which defines a channel extending to the base portion through an inside of the holding section and through an inside of the insertion section, the holding section including a driving source which is driven so as to generate a rotation driving force to rotate the rotary unit, a driving source side actuation portion which is actuated when the driving source is driven, and a driving source side transmission portion which is configured to transmit the generated rotation driving force to the driving source side actuation portion and configured to actuate the driving source side actuation portion when the driving source is driven, the attachment unit being insertable into the channel from the insertion hole and removable from the channel through the insertion hole, and being attached to the insertion section and the holding section when inserted through the channel, the attachment unit comprising:

a line portion which extends through the channel when the attachment unit is attached to the insertion section and the holding section and which is configured to rotate around a driving axis when the attachment unit is attached to the insertion section and the holding section and thereby configured to transmit the rotation driving force to the rotary unit;

an attachment side actuation portion which is configured to receive the rotation driving force from the driving source side actuation portion and configured to be actuated by an actuation of the driving source side actuation portion when the attachment unit is attached to the insertion section and the holding section; and an attachment side transmission portion which is configured to transmit the rotation driving force to the line portion and configured to rotate the line portion around the driving axis in response to an actuation of the attachment side actuation portion when the attachment unit is attached to the insertion section and the holding section.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A driving force transmitting unit in an insertion device, the insertion device including
    an insertion section extending along a longitudinal axis,
    a rotary unit provided to an outer peripheral side of the insertion section rotatably relative to the insertion section in directions around the longitudinal axis,
    a base portion which is provided in the insertion section in a state that the rotary unit is attached rotatably in the directions around the longitudinal axis and which defines a cavity open to an outside and an inside of the insertion section,
    an actuation unit which is attached to the base portion to be located in the cavity and which is actuated in a state that the rotary unit is attached to the base portion, and thereby is configured to transmit a rotation driving force to rotate the rotary unit to the rotary unit,
    a holding section which is provided to a proximal direction side with respect to the insertion section and in which an insertion hole open to an outside of the holding section is formed,
    a driving source unit which is provided in the holding section or removably attached to the holding section, the driving source unit including a driving source which is driven so as to generate the rotation driving force, and
    a channel defining portion which defines a channel extending to the cavity of the base portion from the insertion hole of the holding section through an inside of the holding section and through an inside of the insertion section,
    the driving force transmitting unit being removably attached to the actuation unit in the cavity when inserted through the channel from the insertion hole, the driving force transmitting unit being configured to transmit the rotation driving force to the actuation unit by rotating around a driving axis when the driving force transmitting unit is attached to the actuation unit,
    the driving force transmitting unit comprising:
    a line portion which extends along the driving axis in the channel when the driving force transmitting unit is attached to the actuation unit, and which is insertable into the channel through the insertion hole and removable from the channel through the insertion hole;
    a distal connection portion which is provided in a distal portion of the line portion and which is connected to the actuation unit when the driving force transmitting unit is attached to the actuation unit;
    a slider portion which is attached to the proximal portion of the line portion and which is movable relative to the line portion along the driving axis;
    a driving force receiving portion which is provided in a proximal portion of the line portion or provided to the proximal direction side with respect to the line portion and which is located and set at a position to receive the rotation driving force from the driving source unit and the slider portion is coupled to the holding section; and
    an urging portion having a distal end connected to the line portion and a proximal end connected to the slider portion, the urging portion being configured to contract in response to a movement of the slider portion relative to the line portion toward a distal direction and thereby configured to apply an urging force toward the distal direction to the line portion and the distal connection portion,
    wherein the slider portion is positioned at a first position when the driving force transmitting unit is attached to the actuation unit and the slider portion is coupled to the holding section,
    the slider portion is positioned at a second position when the slider portion is not coupled to the holding section, and
    the slider portion moves relative to the line portion from the second position to the first position toward the distal direction so that the urging portion contracts.

2. The driving force transmitting unit according to claim 1, wherein the driving force receiving portion is located in the slider portion, and
    the driving source unit is removably connected to the driving force receiving portion.

3. The driving force transmitting unit according to claim 2, being inserted through the channel in the insertion device in which the driving source unit is removably attached to the holding section in the insertion hole,
    wherein in an attached state where the driving source unit is attached to the holding section, the slider portion is coupled to the holding section via the driving source unit, and
    in the attached state, the slider portion is pressed from the driving source unit toward the distal direction and is positioned at the first position.

4. The driving force transmitting unit according to claim 3, wherein in an unattached state where the driving source unit is not attached to the holding section, the slider portion protrudes to the outside of the holding section from the insertion hole, and
    in the unattached state, the driving force receiving portion is located outside the holding section.

5. The driving force transmitting unit according to claim 3, wherein in an unattached state where the driving source unit is not attached to the holding section, the urging portion is in a reference state, and
    in the attached state, the urging portion contracts from the reference state.

6. An insertion instrument comprising:
    the driving force transmitting unit according to claim 1;
    the insertion section including the base portion;
    the actuation unit attached to the base portion;
    the holding section provided to the proximal direction side with respect to the insertion section;
    the driving source unit including the driving source which is driven so as to generate the rotation driving force; and
    the channel defining portion defining the channel, through which the driving force transmitting unit is inserted, from the insertion hole of the holding section to the cavity of the base portion.

7. The insertion instrument according to claim 6, wherein the driving source unit includes a driving source side actuation portion which is actuated when the rotation driving force is transmitted from the driving source and which is actuated when the driving force transmitting unit is attached to the actuation unit and thereby configured to transmit the rotation driving force to the driving force receiving portion.

8. The insertion instrument according to claim 6, wherein the distal connection portion of the driving force transmitting unit includes a rotation gear rotatable around the driving axis,
the actuation unit includes a rotary cylindrical body which is rotatable relative to the insertion section in the directions around the longitudinal axis together with the rotary unit, and
the rotary cylindrical body includes an inner peripheral gear portion which is provided over all-round and which meshes with the rotation gear when the driving force transmitting unit is attached to the actuation unit.

9. A rotary unit attached to the insertion instrument according to claim 6,
the rotary unit being attached to the base portion of the insertion section rotatably relative to the insertion section in the directions around the longitudinal axis.

10. An insertion device comprising:
the insertion instrument according to claim 6; and
the rotary unit attached to the base portion of the insertion section rotatably relative to the insertion section in the directions around the longitudinal axis.

11. The insertion instrument according to claim 7, wherein the driving source unit is removably attached to the holding section.

12. The insertion instrument according to claim 7, wherein the driving force transmitting unit includes
an attachment side actuation portion in which the driving force receiving portion is provided and which is actuated when the driving force receiving portion receives the rotation driving force from the driving source side actuation portion, and
an attachment side transmission portion which is configured to transmit the rotation driving force to the line portion from the attachment side actuation portion and configured to rotate the line portion around the driving axis in response to an actuation of the attachment side actuation portion.

13. The insertion instrument according to claim 12, wherein the driving source side actuation portion includes a driving source side rotation portion which is actuated so as to rotate around a transmission rotation axis, and
the attachment side actuation portion includes an attachment side rotation portion which is configured to rotate around the transmission rotation axis when the attachment side actuation portion is actuated by the rotation driving force transmitted to the driving force receiving portion from the driving source side actuation portion.

14. The insertion instrument according to claim 13, wherein the driving force receiving portion is provided in the attachment side rotation portion, and
the driving source side rotation portion includes a driving source side connection portion which is connected to the driving force receiving portion when the driving force transmitting unit is attached to the actuation unit.

15. The insertion instrument according to claim 14, wherein the transmission rotation axis of the driving source side rotation portion and the attachment side rotation portion is coaxial with the driving axis of the line portion when the driving force transmitting unit is attached to the actuation unit, and
the driving source side connection portion is connected to the driving force receiving portion inside the channel.

16. The insertion instrument according to claim 14, wherein the driving source side connection portion is connected to the driving force receiving portion outside the channel.

17. The insertion instrument according to claim 13, wherein the driving source side rotation portion includes a driving source side magnet, and
the attachment side rotation portion includes an attachment side magnet which is configured to rotate the attachment side rotation portion by a magnetic force between the driving source side magnet and the attachment side magnet in response to a rotation of the driving source side rotation portion when the driving force transmitting unit is attached to the actuation unit.

18. The insertion instrument according to claim 17, wherein the driving source side magnet is located inside the holding section, and
the attachment side magnet is located outside the holding section when the driving force transmitting unit is attached to the actuation unit.

19. An insertion body assembly in which the driving force transmitting unit according to claim 1 is inserted through the channel, the insertion body assembly comprising:
the insertion section including the base portion;
the actuation unit attached to the base portion;
the holding section provided to the proximal direction side with respect to the insertion section;
the driving source unit including the driving source which is driven so as to generate the rotation driving force; and
the channel defining portion which defines the channel from the insertion hole of the holding section to the cavity of the base portion.

* * * * *